United States Patent
Kaplan et al.

(10) Patent No.: US 12,331,429 B2
(45) Date of Patent: Jun. 17, 2025

(54) COMPRESSION AND HEAT-ASSISTED PRODUCTION OF SILK-BASED MATERIALS

(71) Applicant: Trustees of Tufts College, Medford, MA (US)

(72) Inventors: David L. Kaplan, Concord, MA (US); Fiorenzo G. Omenetto, Lexington, MA (US); Chunmei Li, Stoneham, MA (US); Chengchen Guo, Wakefield, MA (US)

(73) Assignee: Trustees of Tufts College, Medford, MA (US)

( * ) Notice: Subject to any disclaimer, the term of this patent is extended or adjusted under 35 U.S.C. 154(b) by 1059 days.

(21) Appl. No.: 17/309,005

(22) PCT Filed: Oct. 10, 2019

(86) PCT No.: PCT/US2019/055736
§ 371 (c)(1),
(2) Date: Apr. 12, 2021

(87) PCT Pub. No.: WO2020/117368
PCT Pub. Date: Jun. 11, 2020

(65) Prior Publication Data
US 2021/0381129 A1     Dec. 9, 2021

Related U.S. Application Data

(60) Provisional application No. 62/743,975, filed on Oct. 10, 2018.

(51) Int. Cl.
*D01F 4/02* (2006.01)
*B82Y 40/00* (2011.01)
*C08L 89/00* (2006.01)

(52) U.S. Cl.
CPC .............. *D01F 4/02* (2013.01); *C08L 89/00* (2013.01); *B82Y 40/00* (2013.01); *D10B 2211/04* (2013.01); *D10B 2211/22* (2013.01)

(58) Field of Classification Search
CPC ... D01F 4/02; D10B 2211/04; D10B 2211/22; C08L 89/00; B82Y 40/00
See application file for complete search history.

(56) References Cited

U.S. PATENT DOCUMENTS

2014/0093902 A1\* 4/2014 Omenetto ................ B82Y 5/00
257/40
2015/0283298 A1 10/2015 Kaplan
(Continued)

FOREIGN PATENT DOCUMENTS

JP     H0310019 A     1/1991
JP     2007277481 A    10/2007
(Continued)

OTHER PUBLICATIONS

Daijirou Akiyama et al., "Effect of Preparation Method of Powdered Silk on the Mechanical Properties of Moulded Silk", 2355-2358 (1993).
(Continued)

*Primary Examiner* — Camie S Thompson
(74) *Attorney, Agent, or Firm* — GTC Law Group PC & Affiliates

(57) ABSTRACT

In some embodiments, the present disclosure provides methods including the steps of (i) providing silk fibroin material comprising substantially amorphous structure, and (ii) applying at least one of elevated temperature and elevated pressure to the silk fibroin material to form a silk fibroin article, wherein the applying induces fusion between at least a portion of the silk fibroin and structural change of fibroin in the silk fibroin material. In some embodiments, the (Continued)

present disclosure also provides silk fibroin articles made in accordance with the methods disclosed herein.

16 Claims, 33 Drawing Sheets

(56) References Cited

U.S. PATENT DOCUMENTS

| | | | |
|---|---|---|---|
| 2016/0046679 A1* | 2/2016 | Kluge | C07K 14/43518 428/221 |
| 2016/0089854 A1 | 3/2016 | Omenetto | |
| 2016/0237128 A1* | 8/2016 | Omenetto | B23K 26/361 |
| 2016/0263228 A1 | 9/2016 | Kluge | |

FOREIGN PATENT DOCUMENTS

| | | | |
|---|---|---|---|
| WO | 2005012606 A2 | | 2/2005 |
| WO | WO2005103158 | * | 3/2008 |
| WO | 2014125505 A4 | | 11/2014 |
| WO | 2017047503 A1 | | 3/2017 |
| WO | 2020117368 A2 | | 6/2020 |

OTHER PUBLICATIONS

Yongzhen Tao et al., "Structure and Properties of Composites Compression-molded from Silk Fibroin Powder and Waterborne Polyurethane", 639-644 (2011).
Altman, G. H. et al. Silk-based Biomaterials. Biomaterials 24, 401-416 (2003).
Cebe, P. et al. Beating the Heat—Fast Scanning Melts Silk Beta Sheet Crystals. Sci. Rep. 3, 741-7 (2013).
Cheng, G., et al. Differences in regenerated silk fibroin prepared with different solvent systems: From structures to conformational changes. Journal of Applied Polymer Science 132.22 (2015).
Ha, S.-W., et al. Dissolution of Bombyx mori silk fibroin in the calcium nitrate tetrahydrate-methanol system and aspects of wet spinning of fibroin solution. Biomacromolecules 4, 488-496 (2003).
Ha, S.-W., et al. Structural studies of Bombyx mori silk fibroin during regeneration from solutions and wet fiber spinning. Biomacromolecules 6, 1722-1731 (2005).
Hu, X., et al. "Dynamic protein-water relationships during ß-sheet formation." Macromolecules 41.11 (2008): 3939-3948.
Hu, X., et al. "Effect of water on the thermal properties of silk fibroin." Thermochimica Acta 461.1-2 (2007): 137-144.
Hu, X., et al. Determining Beta-Sheet Crystallinity in Fibrous Proteins by Thermal Analysis and Infrared Spectroscopy. Macromolecules 39, 6161-6170 (2006).
International Searching Authority. International Search Report and Written Opinion for application PCT/US2019/055736. Mailed on May 28, 2020. 10 pages.
Kluge, J. A., et al. Optimizing molecular weight of lyophilized silk as a shelf-stable source material. ACS Biomater. Sci. Eng. 2, 595-605 (2016).
Koebley, S. R. et al. Silk Reconstitution Disrupts Fibroin Self-Assembly. Biomacromolecules 16, 2796-2804 (2015).
Koh, L.-D. et al. Structures, mechanical properties and applications of silk fibroin materials. Prog. Polym. Sci. 46, 86-110 (2015).
Krywka, C., et al. Determination of silkworm silk fibroin compressibility using high hydrostatic pressure with in situ X-ray microdiffraction. Macromolecules 47, 7187-7193 (2014).
Kundu, B., et al. Silk fibroin biomaterials for tissue regenerations. Advanced Drug Delivery Reviews 65, 457-470 (2013).
Lee, K. H. "Silk sericin retards the crystallization of silk fibroin." Macromolecular rapid communications 25.20 (2004): 1792-1796.
Lefevre, T., et al. Protein Secondary Structure and Orientation in Silk as Revealed by Raman Spectromicroscopy. Biophys. J. 92, 2885-2895 (2007).
Li, C. et al. Regenerated silk materials for functionalized silk orthopedic devices by mimicking natural processing. Biomaterials 110, 24-33 (2016).
Lu, Q. et al. Silk Self-Assembly Mechanisms and Control From Thermodynamics to Kinetics. Biomacromolecules 13, 826-832 (2012).
Marelli, B. et al. Programming function into mechanical forms by directed assembly of silk bulk materials. Proc. Natl. Acad. Sci. USA 114, 451-456 (2017).
Marsh, R. E., et al. An Investigation of the Structure of Silk Fibroin. Biochim. Biophys. Acta 16, 1-34 (1955).
Pauling, L. et al. Configurations of Polypeptide Chains with Favored Orientations Around Single Bonds: Two New Pleated Sheets. Proc. Natl. Acad. Sci. U.S.A. 37, 729-740 (1951).
Perrone, G. S. et al. The use of silk-based devices for fracture fixation. Nat. Commun. 5, 1-9 (2014).
Qiao, X., et al. "Effect of electron beam irradiation on the crystallization of silk fibroin fiber-reinforced poly (e-caprolactone) biocomposites." Polymer international 59.4 (2010): 447-455.
Rockwood, D. N. et al. Materials fabrication from Bombyx mori silk fibroin. Nat. Protoc. 6, 1612-1631 (2011).
Sidhu, M. S., et al. The processing and heterostructuring of silk with light. Nat. Mater. 16, 938-945 (2017).
Trabbic, K. A. et al. Comparative structural characterization of naturally- and synthetically-spun fibers of Bombyx mori fibroin. Macromolecules 31, 462-471 (1998).
Um, I. C., et al. Structural characteristics and properties of the regenerated silk fibroin prepared from formic acid. Int. J. Biol. Macromol. 29, 91-97 (2001).
Vepari, C. et al. Silk as a biomaterial. Prog. Polym. Sci. 32, 991-1007 (2007).
Wray, L. S. et al. Effect of processing on silk-based biomaterials: reproducibility and biocompatibility. J. Biomed. Mater. Res. Part B Appl. Biomater. 99, 89-101 (2011).
Yamaguchi, K. et al. Primary Structure of the Silk Fibroin Light Chain Determined by cDNA Sequencing and Peptide analysis. J. Mol. Biol. 210, 127-139 (1989).
Zhou, C. et al. Silk Fibroin: Structural Implications of a Remarkable Amino Acid Sequence. Proteins: Struct., Funct., Genet. 44, 119-122 (2001).
19893001.8, "European Application Serial No. 19893001.8, Extended European Search Report mailed Jun. 21, 2022", Tufts University, 4 pages.
Akiyama, Daijirou , "Effect of preparation method of powdered silk on the mechanical properties of moulded silk", Polymer, vol. 35, 1994, pp. 2355-2358.
Guo, Chengchen , et al., "Thermoplastic moulding of regenerated silk", Nature Materials, Nature Publishing Group UK, London, vol. 19, No. 1, Dec. 16, 2019, pp. 102-108.
PCT/US2019/055736 , "International Application Serial No. PCT/US2019/055736, International Preliminary Report on Patentability mailed Apr. 8, 2021", Tufts University, 7 pages.

\* cited by examiner

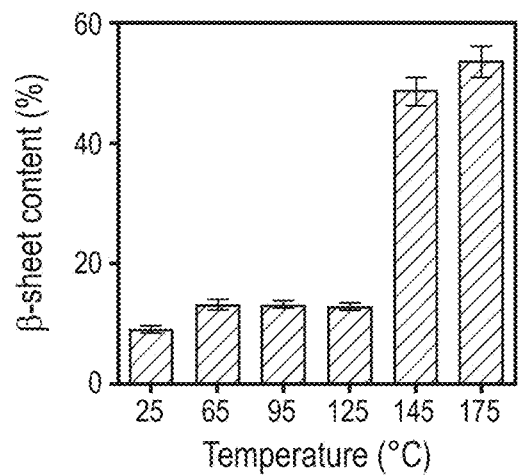 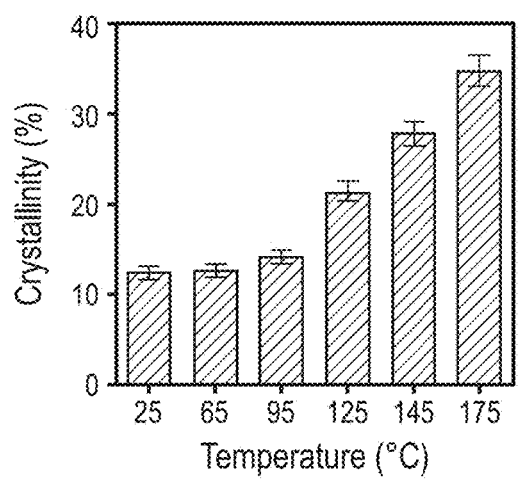
FIG. 8D  FIG. 8E
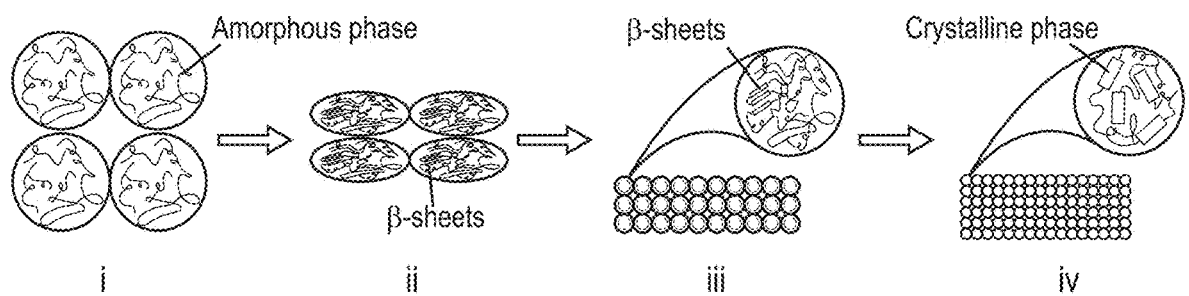
FIG. 8F

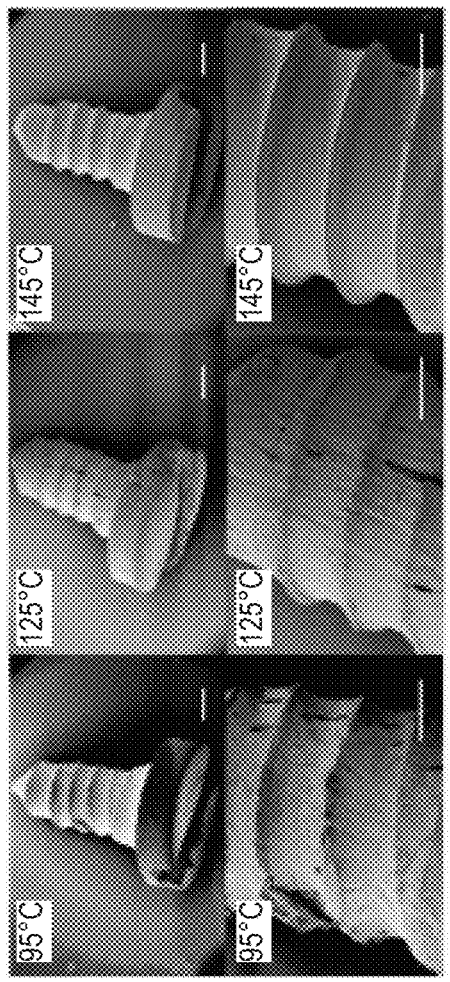
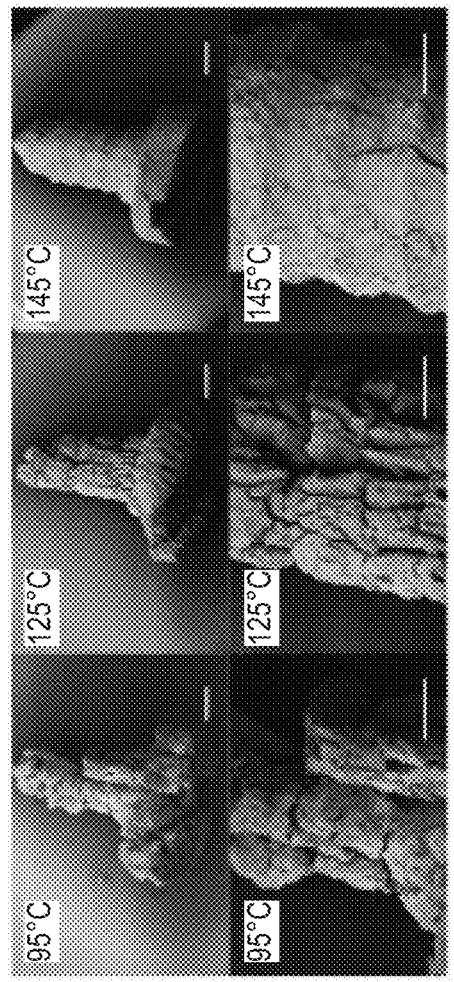
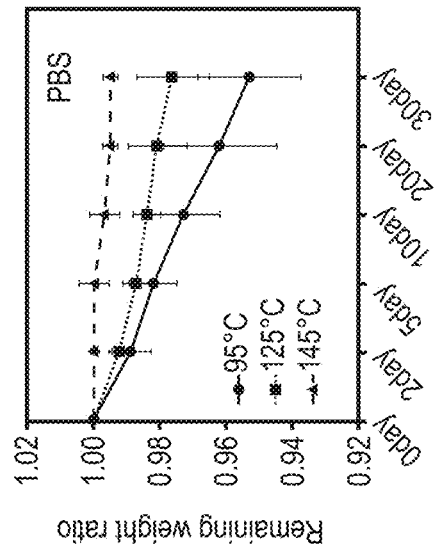
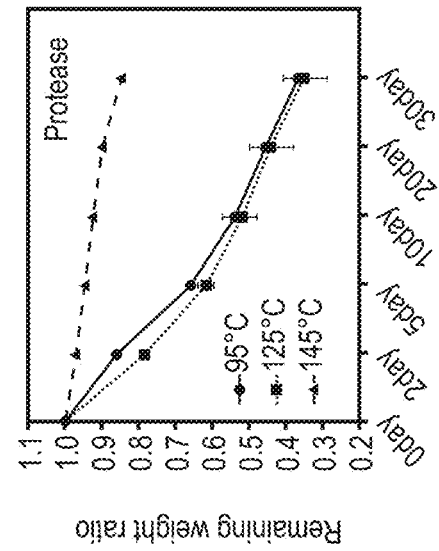
FIG. 15A
FIG. 15B

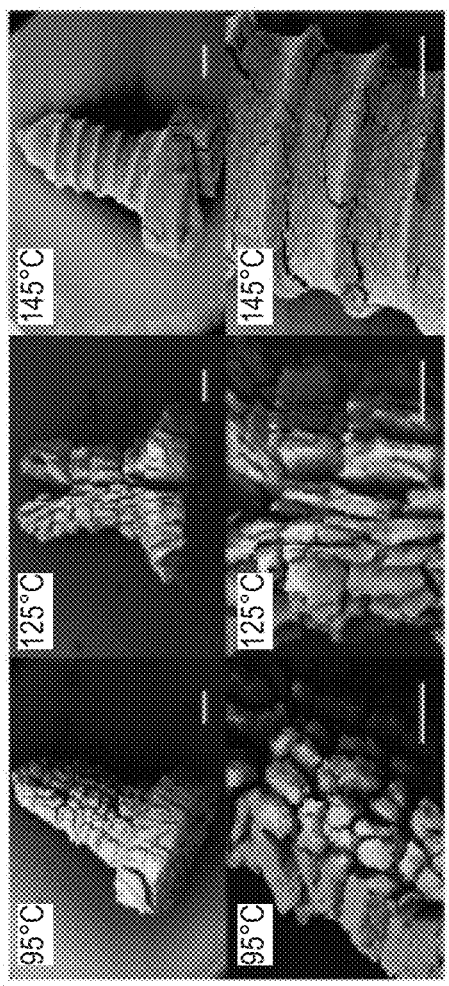
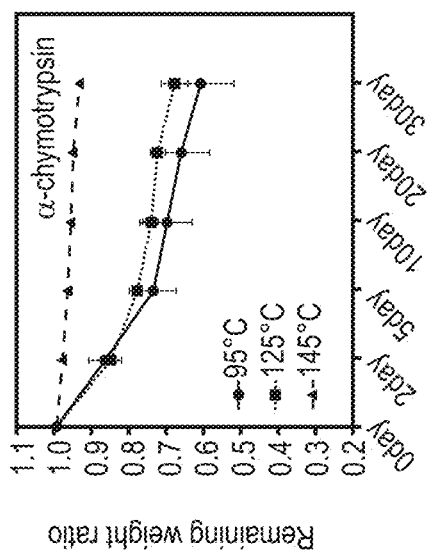
FIG. 15C

| Residue | Liquid Silk in Gland [1] | Regenerated Silk Solution (this work) | Degummed Silk | Lyophilized Silk |
|---|---|---|---|---|
| Gly Cα | 43.0 | 43.0 | 43.3 | 43.2 |
| Gly CO | 171.9 | - | 169.5 | 171.0 |
| Gly NH | 107.5/107.9/110.8 | 107.5/107.9/110.8 | - | - |
| Ala Cα | 50.5 | 50.5 | 49.6 | 50.8 |
| Ala Cβ | 16.9 | 16.9 | 17.3/20.8 | 16.6 |
| Ala CO | 175.9 | - | 172.8 | 173.9 |
| Ala NH | 123.5 | 123.5 | - | - |
| Ser Cα | 56.3 | 56.4 | 55.3 | 56.2 |
| Ser Cβ | 61.7 | 61.7 | 63.8 | 61.6 |
| Ser CO | 173.0 | - | 170.9 | 171.8 |
| Ser NH | 114.7/115.3 | 114.7/115.3 | - | - |
| Tyr Cα | 56.1 | 56.0 | 54.7 | 56.4 |
| Tyr Cβ | 36.6 | 36.5 | 36.3/40.5 | 36.3 |
| Tyr Cγ | 128.4 | - | 127.4 | 127.3 |
| Tyr Cδ | 130.9 | 131.0 | 130.3 | 130.6 |
| Tyr Cε | 115.8 | 116.0 | 115.3 | 115.4 |
| Tyr Cζ | 155.0 | - | 155.8 | 156.0 |
| Tyr CO | 173.0 | - | 171.2 | 173.3 |
| Tyr NH | 119.8 | 119.8 | - | - |

FIG. 22

|  | HFIP-methanol method | Sol-gel-solid method | Heat and high pressure assisted method |
| --- | --- | --- | --- |
| Time | ~21 days<br>Silk processing: 3-4 days<br>Freeze-dry: 2-3 days<br>HFIP dissolving and methanol treatment: 3-4 days<br>Post treatment/drying: 12 days | ~19 days<br>Silk processing: 3-4 days<br>Slow drying: 14-16 days | ~6 days<br>Silk processing: 3-4 days<br>Freeze-dry: 2-3 days<br>Hot press: 0.5 h |
| Cost | $5.4/g | $0.8/g | $0.8/g |
| Toxicity | Toxic | Nontoxic | Nontoxic |
| Tunability | No | No | Yes |

FIG. 27

Heavy chain (5263 residues, 391,593 Da)

MRVKTFVILCCALQYVAYTNANINDFDEDYFGSDVTVQSSNTTDEIIRDASGAVIEEQITTKKMQRKNKNIHGILGKNEKMIKTEFVITTDSDGNESIVEEDVLM
KTLSDGTVAQSYVAADAGAYSQSSGPYVSNSGYSTHQGYTSDFSTSAAV (N-terminal)
GAGAGAGAAAGSGAGAQAGYGAASGAGAGAGAGAGAGYGTGAQAGAGAGYGAGAGAGAGAGYGAGAGAGAGAGYGAGAGAGAGAGYGAGAGAG
AGAGYGAGAGAGAGYGAASGAGAGAGYGQGVGSGAASGAGAGAGAGSAAGSGAGAGAGTGAGAGYQAGAGAGAGAGYGAASGTGAGYGAGGA
GAGYGGASGAGAGAGAGAGAGAGYGTGAGYGAGAGAGAGAGAGYGAGAGAGYGAGYGVGAGAGYGAGYGAGAGSGAASGAGSGAGAGS
GAGAGSGAGAGSGAGAGSGAGAGSGAGAGSGTGAGSGAGAGYGAGAGAGYGAGAGSGAASGAGAGSGAASGAGAGSGAGAGSGAGAGSGA
GAGSGAGAGSGAGAGYGAGAGAGYGAGAGAGTGAGAGTGAGAGVGTGAGSGAASGAGAGSGAGAGSGAGAGSGAGAGSGASGAGAGS
GAGAGSGAGAGSGAGVGYGAGVGAGYGAGYGAGAGYGAGAGSGAAS
GAGAGAGAGAGTGSSGFGPYVAGGUSRSDGUEUAWSSDFGTGS (Linker)
GAGAGSGAGAGSGAGAGSGAGAGSGAGAGSGAGAGSGAGAGSGAGVGYGVGYGAGYGAGAGAGYGAGAGSGAASGAGAGSGAGAGSGAGAGSGAGAGSGA
GAGSGAGAGSGAGAGSGAGAGSGAGAGSGAGAGSGAGAGSGAGAGSGAGVQSGAGAGSGAGAGVGYGAGAGVGYGAGAGSGAASGAGAGSGAGAGSGAGAGSGA
GSGAGAGSGAGAGSGAGAGSGAGAGSGAGAGSGAGAGSGAGAGSGAGVGYGAGVGAGYGAGYGAGAGAGYGAGAGSGAASGAGAGSGAGAGSGAGAGSGAGA
GSGAGAGSGAGAGSGAGAGSGAGAGSGAGAGSGAGAGSGAGAGSGAGAGYGAGYGAGAGAGYGAGAGSGAASGAGAGSGAGAGSGAGAGSGA
GAGSGAGAGSGAGAGSGAGAGSGAGAGSGAGAGSGAGAGSGAGVGYGAGYGAGVGYGAGAGAGYGAGAGSGAASGAGAGSGAGAGSGAGAGSGAGAGSGA
GAGSGAGAGSGAGAGSGAGAGSGAGAGSGAGVGYGAGYGAGAGAGYGAGAGSGAAS
GAGAGAGAGAGTGSSGFGPYVAHGGYSGYEYAWSSESDFGTGS (Linker)
GAGAGSGAGAGSGAGAGSGAGAGSGAGAGSGAGYGAGVGAGYGAGYGAGAGAGYGAGAGSGAGSGAGAGSGAGAGSGAGAGSGAGAGSGAGAGSGAGAGSGA
GSGAGAGSGAGAGSGAGAGSGAGAGSGAGAGSGAGYGAGYGAGAGAGYGAGAGSGAGSGAGAGSGAGAGSGAGAGSGAGAGSGAGAGSGAGAGSGAGAGSGAGAGSGAGAGYGA
GVGAGYGAGYGAGAGAGYGAGAGSGAGAGSGAGAGSGAGAGSGAGVGSGAGAGSGAGAGSGAGAGSGAGAGSGAGAGSGAGAGYGAGYGAGAGAGYGAGA
GSGAGAGSGAGAGSGAGAGSGAGSGAGAGSGAGAGSGAGAGSGAGAGSGAGAGSGAGVGYGAGVGAGYGAGYGAGAGYGAGAGSGAAS
GAGAGAGAGAGTGSSGFGPYVANGGYSGYEYANSSESDFGTGS (Linker)
GAGAGSGAGAGSGAGAGSGAGAGSGAGAGSGAGAGYGAGYGAGAGYGAGYGAGAGAGYGAGAGSGAGSGAGAGSGAGAGSGAGAGSGAGAGSGAGAGSGAGAGSGAGAGSGAGA
GSGAGSGSGAGAGSGAGAGSGAGAGYGAGYGAGAGYGVGYGAGAGAGYGAGAGSGAAS
GAGAGAGAGAGTGSSGFGPYVAHGGYSGYEYAWSSESDFGTGS (Linker)
GAGAGSGAGAGSGAGAGSGAGAGSGAGAGSGAGAGSGAGAGSGAGAGYGAGYGAGYGAAYGAGAGAGYGAGAGSGAASGAGAGSGAGAGSGAGAGSGAGAGSGAG
AGSGAGAGSGAGAGSGAGAGSGAGAGSGAGAGSGAGAGSGAGAGSGAGAGYGAGAGYGAGAGSGAGSGAGAGSGAGAGSGAGAGSGAGAG
SGAGSGAGAGSGAGAGSGAGAGYGAFVGAGYGAGYGAGAGAGYGAGAGSGAGAGSGAGAGSGAGAGSGAGAGYGAGYGAGAGAGYGAGAG
TGAGSGAGAGSGAGAGSGAGAGSGAGAGSGAGAGSGAGAGSGAGSGAGAGSGAGAGSGAGAGSGAGAGSGAGAGSGAGAGAGYGAGAGAGYG
AGYGAGAGYGAGAGSGAGSGAGAGSGAGAGSGAGAGSGAGAGYGAGYGAGAGSGAAS
GAGAGAGAGAGTGSSGFGPYVAHGGYSGYEYAWSSESDFGTGS (Linker)
GAGAGSGAGAGSGAGAGYGAGVGAGYGAGYGAGAGYGAGAGSGTGSGAGAGSGAGAGYGAGVGAGYGAGAGSGAAFGAGAGAG
SGAGAGSGAGAGSGAGAGSGAGAGSGAGAGSGAGAGYGAGYGAGVGAGYGAGAGSGAASGAGAGSGAGAGSGAGAGSGAGAGSGAGAGSGAGAGSGAGAGYGAGV
GAGYGAGYGAGAGAGYGAGAGSGAASGAGAGSGAGAGSGAGAGSGAGAGSGAGAGSGAGAGSGAGSGAGAGSGAGAGSGAGAGSGAGAGYGAGAGSGAAS
GAGAGAGAGTGSSGFGPYVANGGYSGYEYAWSSESDFGTGS (Linker)
GAGAGSGAGAGSGAGAGSGAGAGSGAGAGSGAGYGAGVGAGYGAGAGAGYGAGAGSGAGSGAGAGSGAGAGSGAGAGSGAGAGSGAGAGSGA
GAGSGAGAGYGAGAGSGAASGAGAGSGAGAGSGAGAGSGAGAGSGAGAGSGAGAGSGAGAGSGAGAGSGAGAYGAGVGAGYGVGYGAGAGAGYGAGAGSGAGS
GAGAGSGAGAGSGAGAGSGAGAGSGAGAGSGAGAGSGAGSGAGAGSGAGAGSGAGAGSGAGAGSGAGAGYGVGYGAGAGAGYGAGAGSGAGSGAGAGSGA
GAGSGAGAGSGAGAGSGAGAGSGAGAGYGAGVGAGYGVGYGAGAGAGYGAGAGSGAGAGSGAGAGSGAGAGSGAGAGYGAGVGAGYGVGYGAGVGA
GYGAGAGSGAASGAGAGSGAGAGSGAGAGSGAGAGSGAGAGSGAGAGSGAGAGYGAGYGAGVGAGYGVGYGAGAGAGYGA
GAGSGAASGAGAGAGSGAGAGTGAGAGSGAGAGSGAAS
GAGAGSGAGAGTGSSGFGPYVANGGYSGYEYAWSSESDFGTGS (Linker)
GAGAGSGAGAGSGAGAGSGAGAGSGAGAGSGAGAGYGAGVGAGYGAGAGSGAGSGAGAGSGAGAGSGAGAGSGAGAGSGAGAGSGAGAGYGAGAGSGTGSGAGA
GSGAGAGSGAGAGSGAGAGSGAGAGSGAGAGYGAGVGAGYGVGYGAGAGAGYGAGAGSGAGSGAGAGSGAGAGSGAGAGSGAGAGSGAGAGSGAGSGAGAGSGA
GAGSGAGAGSGAGAGSGAGAGYGAGVGAGYGVGYGAGAGAGYGAGAGSGAGSGAGAGSGAGAGSGAGAGSGAGAGSGAGAGSGAGSGAGAGSGAGAGS
GAGAGSGAGAGSGAGAGSGAGAGYGVGYGAGAGAGYGAGAGSGAGSGAGAGSGAGAGSGAGAGSGAGAGSGAGSGAGAGSGAGAGSGAGAGYGA
GVGAGYGVGYGAGAGAGYGAGAGSGAGSGAGAGSGAGAGSGAGAGSGAGAGSGAGAGSGAGSGAGAGSGAGAGSGAGAGYGA
GAGAGYGAGVGAGYGVGYGAGAGAGYGAGAGSGAAS
GAGAGAGAGTGSSGFGPYVANGGYSGYEYAWSSESDFGTGS (Linker)
GAGAGSGAGAGSGAGAGSGAGAGSGAGAGSGAGAGYGAGVGAGYGAGAGVGAGAGYGAGAGSGAASGAGAGAGAGAGSGAGAGSGAGAGSGAGAGAGSGAGAGYGAFY
GIGVGAGYGAGAGVGYGAGAGSGAGAGSGAGAGSGAASGAGAGAGAGAGSGAGAGSGAGAGSGAGAGSGAGAGSGAGAGSGAGAGYGAGYGAGVGAGYGAGAG
VGYGAGAGAGYGAGAGSGAASGAGAGAGAGAGSGAGAGSGAGAGSGAGAGSGAGAGSGAGAGSGAGAGSGAGAGSGAGAGYGAGAGSGAAS
GAGAGAGAGTGSSGFGPYVNGGYSGYEYAWSSESDFGTGS (Linker)
GAGAGSGAGAGSGAGAGSGAGAGSGAGAGYGAGVGAGYGAGYGAGAGAGYGAGAGSGAASGAGAGSGAGAGSGAGAGSGAGSGAGAGSGAGAGA
GSGAGAGSGAGAGSGAGAGSGAGAGYGAGVGAGYGVGYGAGAGAGYGAGAGSGAASGAGAGSGAGAGSGAGAGSGAGAGSGAGAGSGAGAGSGAGA
GSGAGAGSGAGSGAGAGSGAGAGSGAGYGAGVGAGYGVGYGAGAGAGYGAGAGSGAASGAGAGSGAGAGSGAGAGSGAGAGSGAGAGSGAGAGAGSGAGA
GSGAGAGYGAGYGAGVGAGYGAGAGSGAAS
GAGAGAGAGTGSSGFGPYVANGGYSGYEYAWSSESDFGTGS (Linker)
GAGAGSGAGAGSGAGAGYGVGYGAGYGAGYGAGAGAGYGAGAGSGAGSGAGAGSGAGAGSGAGAGSGAGAGSGAGAGSGAGAGSGAGAGSGAGAGSGA
GAGYGAGAGAGYGAGAGVGYGAGAGAGYGAGAGSGAGSGAGAGSGSGAGAGSGSGAGSGAGAGSGAGAGSGAGAGSGAGAGSGAGAGSGAGAGS
GAGAGSGAGAGYGAGYGIGVuGAGVGYGAGAGAGSGAASGAGAGSGAGAGSGAGAGSGAGAGSGAGAGSGAGAGSGAGAGSGAGAGSGAGAGSGAGAGS
GAGAGYGAGAGVGYGAGAGSGAASGAGAGSGAGAGSGAGAGSGAGAGSGAGAGSGAGAGSGAGSGAGSGAGSGAGAGSGAGAGYGAGYGAGVGA
GYGAGAGYGVGAGAGYGAGAGSGAGSGAGAGSGAGAGSGAGAGSGAGAGSGAGAGSGAGAGSGAGSGAGAGYGAGAGYGAGAGYGAGAGS
GAASGAGAGAGAGSGAGAGSGAGAGSGAGSGAGAGSGAGAGYGAGAGSGAASGAGAGSGAGAGAGAGAGSGAGAGSGAGAGSGAGAGYGAGSGAA
S
GAGAGAGAGTGSSGFGPYVANGGYSRREGYEYAWSSKSDFETGS (Linker)
GAASGAGAGAGSGAGAGSGAGAGSGAGAGSGAGAGS
VSYGAGRGYGQGAGSAASSVSSASSRSYDYSRRNVRKNCGIPRRQLVVKFRALPCVNC (C-terminal)

a: GAGAGA y: GAGAGY s: GAGAGS u: GAGYGA

Light chain (262 residues, 27669 Da)

MKPIFLVLLVATSAYAAPSVTINQYSDNEIPRDIDDGKASSVISRAWDYVDDTDKSIAILNVOEILKDMASQGDYASQASAVAQTAGILAHLSAGIPGDACAAAN
VINSYTDGVRSGNFAGFRQSLGPFFGHVGQNLNLINQLVINPGQLRYSVGPALGCAGGGRIYDFEAAWDAILASSDSSFLNEEYCIVKRLYNSRNSQSNNI
AAYITAHLLPPVAQVFHQSAGSITDLLRGVGNGNDATGLVANAQRYIAQAASQVHV

FIG. 29

COMPRESSION AND HEAT-ASSISTED PRODUCTION OF SILK-BASED MATERIALS

CROSS-REFERENCE TO RELATED APPLICATIONS

This application is a national stage application, filed under 35 U.S.C. § 371, of International Patent Application PCT/US2019/055736, filed Oct. 10, 2019, and is related to and claims priority to U.S. Provisional Patent Application 62/743,975, filed Oct. 10, 2018, the contents of each of which are incorporated herein by reference for all purposes.

STATEMENT REGARDING FEDERALLY FUNDED RESEARCH

This invention was made with government support under grants AR068048 and DE016525 awarded by the National Institutes of Health and grant FA9550-17-1-0333 awarded by the United States Air Force. The government has certain rights in the invention.

BACKGROUND

Silks are generally defined as protein polymers that are produced naturally by some Lepidoptera larvae such as silkworms, spiders, scorpions, and flies. Silkworm silk has been used commercially in textile production for centuries and it is recognized as one of the most studied protein-based materials in history. Silkworm silk and spider silk are the most studied and widely used, and are excellent materials for biomedical applications such as drug delivery and tissue engineering because of their biocompatibility, biodegradability, and extraordinary mechanical properties. Silkworm silk has been used as suture material for centuries and recently has gained considerable attention as a biomaterial with various medical applications due to its tunable degradation rate in vivo and its ability to be fabricated into multiple types of materials such as fibers, films, gels, and foams. However, comparing to the traditional polymer industry, there are very limited developed technologies for processing silk and production of silk-based materials.

SUMMARY

Compositions and methods described herein relate to, inter alia, production of silk-based materials using a novel compression and thermal based method. The silk-based materials herein include pure silk materials (e.g., silk film, silk monolithic materials) and/or composite materials (e.g., silk-graphene composites, silk-enzyme composites). The processes provided herein are shown to generate a variety of silk materials with properties comparable, or even superior, to those of the materials fabricated by solution-based processes, such as transparent silk films, silk orthopedic devices and functional silk patterns. Moreover, in some embodiments, these processes can be used to fabricate functional silk formats that cannot be attained by solution-based processes, such as silk materials with controllable degradability by incorporating silk-degrading enzymes and conductive silk-graphene composites. In some embodiments, the fabrication techniques described here can be extended to other structural biopolymers like collagens and recombinant silk proteins.

In some embodiments, the present disclosure provides methods including the steps of (i) providing silk fibroin material comprising substantially amorphous structure, and (ii) applying at least one of elevated temperature and elevated pressure to the silk fibroin material to form a silk fibroin article, wherein the applying induces fusion between at least a portion of the silk fibroin and structural change of fibroin in the silk fibroin material. In some embodiments, a silk fibroin material is transformed into a solid silk article that has undergone a silk conformational change that includes at least some of the silk fibroin being fused together.

In some embodiments, the present disclosure provides methods including the steps of (i) selecting an elevated temperature and an elevated pressure to produce a desired silk fibroin article of a desired crystallinity and desired material properties; and (ii) applying the elevated temperature and the elevated pressure to a silk fibroin material comprising substantially amorphous structure to form a silk fibroin article, wherein the silk fibroin article has the desired crystallinity and the desired material properties.

In some embodiments, the present disclosure also provides silk fibroin articles made in accordance with the methods disclosed herein. In some embodiments, a silk fibroin article is or comprises a packaging material. In some embodiments, a packaging material is suitable for use in fabricating electronic devices, drug delivery system, patterning, molding, and any combination thereof. In some embodiments, a silk fibroin article comprises semi-crystalline silk fibroin, wherein the silk fibroin article has a glass transition temperature between about 40° C. to 135° C. In some embodiments, provided compositions provided compositions include both crystalline silk fibroin and non-crystalline silk fibroin. In some embodiments, the flexural strength of a silk fibroin article is at least 5 MPa and density of substantially the entire silk fibroin article is at least 1.20 g/cm$^3$. In some embodiments, a silk fibroin article comprises silk in an amount of about 10% (w/w) or higher. In some embodiments, a silk fibroin article degrades at least 1 wt % after 30 days of exposure to an aqueous environment at 37° C.

In various embodiments, the present disclosure encompasses the discovery that application of certain combinations of elevated temperature and/or elevated pressure can result in the crystallization of silk molecules in a silk fibroin material. In some embodiments, crystallization may include a transition from an amorphous state to a semi-crystalline or crystalline structure and/or □-sheet structure. In some embodiments, applying elevated temperatures and/or pressures may result in an increase in the amount of β-sheet in the silk fibroin article of at least 1% as compared to the level of β-sheet in the silk fibroin material. In some embodiments, an applying step results in an increase in the amount of β-sheet in the silk fibroin article of at least 50% as compared to the level of β-sheet in the silk fibroin material. As is discussed herein, the present disclosure provides an array of new methods for providing silk fibroin articles including the application of each of: at least one period of exposure of a silk fibroin material to an elevated temperature, and at least one period of exposure of a silk fibroin material to an elevated pressure. In some embodiments, an elevated temperature and an elevated pressure are applied simultaneously. In some embodiments, an elevated temperature is applied to the silk fibroin material after an elevated pressure is applied. In some embodiments, an applying step occurs, at least in part, in a mold. In some embodiments, an applying does not occur in a mold.

As is discussed herein, the present disclosure provides an array of new methods for providing silk fibroin articles including the application of each of: at least one period of exposure of a silk fibroin material to an elevated temperature, and at least one period of exposure of a silk fibroin material to an elevated pressure. In some embodiments, an elevated temperature and an elevated pressure are applied simultaneously. In some embodiments, an elevated temperature is applied to the silk fibroin material after an elevated pressure is applied. In some embodiments, an applying step occurs, at least in part, in a mold. In some embodiments, an applying does not occur in a mold.

In some embodiments, an applying step is or comprises heat pressing. In some embodiments, heat pressing occurs at a pressure that is at least 1 MPa. In some embodiments, heat pressing occurs at temperature that is between 25° C. to 200° C.

In some embodiments, a silk fibroin article is substantially transparent. In some embodiments, a silk fibroin article is bioresorbable. In some embodiments, a silk fibroin article has thermal forming properties and can be reformed to desirable shapes at elevated temperatures or elevated pressures.

The present disclosure also encompasses, in some embodiments, compositions including one or more additives (e.g., 2, 3, 4, 5, 6, 7, 8, 9, 10 or more additives). In some embodiments, and additive may enhance one or more properties of a provided composition (e.g., a physical property, a mechanical property, etc). In some embodiments, a silk fibroin material is mixed with at least one additive prior to the applying step, to form a composite silk fibroin article. In some embodiments, an additive is or comprises at least one of small organic or inorganic molecules, organic macromolecules, inorganic macromolecules, biological macromolecules, e.g., peptides and proteins; electrically conductive materials, carbon-based materials, antibodies and antigen binding fragments thereof; antigens; nucleic acids; nucleic acid analogs and derivatives; sugars; immunogens; natural compounds and extraction from biological systems such as cells, bacterias, or tissues; synthetic materials; metallic materials; alloys; hydrophobic materials; hydrophilic materials; nanomaterials; and any combination thereof. In some embodiments, an organic macromolecule is or comprises at least one enzyme, e.g., protease. In some embodiments, the activity of an enzyme is stabilized by silk at elevated temperature and pressure. In some embodiments, a protease is or comprises one or more of the following: Protease XIV, Proteinase K, α-chymotrypsin, collagenase, matrix metalloproteinase-1 (MMP-1) and MMP-2. In some embodiments, an electrically conductive material is or comprises an inorganic conductive material (e.g., silver, gold, iron oxide), an organic conductive material (e.g., graphene), a metal, an alloy, a semiconductor material and/or a conjugated polymer. In some embodiments, an additive is mixed with the silk fibroin material at a ratio between 0.001 wt % and 95.0 wt %.

Provided methods and compositions (e.g., articles) may include one or more physical and/or mechanical properties that are not observed when using previously known methods. By way of example, in some embodiments, a silk fibroin article is substantially homogeneous. In some embodiments, a provided silk article is considered substantially homogenous if it exhibits a consistent structure across the majority of the article (e.g., at least 70%, 80%, 90%, 95% or more of a silk article exhibits a consistent structural pattern).

Further, in certain embodiments, provided methods allow for the production of complex articles using techniques that, when applied using previous methods would result in a significantly different article (e.g., in terms of physical and/or mechanical properties). In accordance with several embodiments, the provided methods may be used to produce any of a variety of silk fibroin articles. In some embodiments, a silk fibroin article may be or comprise comprise a film, a fiber, a mesh, a needle, a tube, a plate, a screw, a rod or any desired shape.

Further, in certain embodiments, provided methods allow for the production of complex articles using techniques that, when applied using previous methods would result in a significantly different article (e.g., in terms of physical and/or mechanical properties). In accordance with several embodiments, the provided methods may be used to produce any of a variety of silk fibroin articles. In some embodiments, a silk fibroin article may be or comprise comprise a film, a fiber, a mesh, a needle, a tube, a plate, a screw, a rod or any desired shape.

Provided methods and compositions allow for the production of silk articles exhibiting one or more enhanced properties. In some embodiments, a silk fibroin article may have enhanced thermal or electrical properties. In some embodiments, a silk fibroin article is electrically conductive. In accordance with various embodiments, provided compositions may be amenable to patterning (e.g., on a surface of a composition).

In some embodiments, provided compositions may be biocompatible and/or biodegradable. In accordance with various embodiments, provided methods and compositions allow for any of a variety of degradation profiles which, in turn, allow for a wide variety or potential applications. For example, in some embodiments, a silk article degrades at least 50 wt % after about 96 hours of exposure to an aqueous environment at 37° C. By way of additional example, in some embodiments, a silk fibroin article does not degrade more than 10% after 6 months of exposure to an in vivo environment or condition.

Any of a variety of forms of silk fibroin material may be used in accordance with various provided methods and compositions. In general, any silk fibroin material that comprises a substantial amount of amorphous silk may be used in accordance with some embodiments. By way of non-limiting example, in some embodiments, a silk fibroin material may be or comprise particles, films, and/or fibers. In some embodiments, particles may be or comprise at least one of microparticles and nanoparticles.

In some embodiments, a provided silk article may be prepared by a process including a step where a silk fibroin material is transformed into a solid silk article that has undergone a silk conformational change that includes at least some of the silk fibroin being transformed from an amorphous state to a semi-crystalline structure.

Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTIONS OF THE DRAWINGS

FIG. 1 panel (a) shows natural degummed silk fibers. Panels (b) and panel (c) show SEM images of natural degummed silk fibers. Panel (d) shows amorphous silk nanomaterials. Panels (e) and (f) show SEM images of amorphous silk nanomaterials. Panel (g) shows X-ray diffraction (XRD) profiles of degummed silk fiber and amorphous silk nanomaterials. Panel (h) shows a solid-state NMR spectra of degummed silk fiber and amorphous silk nanomaterials. Panel (i) shows an FTIR spectra of degummed silk fiber and amorphous silk nanomaterials. Panel (j) shows quantitative analysis of secondary structures present in degummed silk fiber and amorphous silk nanomaterials.

FIG. 2 in panel (A), shows exemplary Thermal Gravimetric Analysis (TGA) profiles and differential thermogravimetric (DTG) analysis of lyophilized silk powder and degummed silk fiber. Panel (B) shows exemplary Differential Scanning calorimetry (DSC) profiles of lyophilized silk powder and degummed silk fiber. Heating rate is 10° C./min for TGA, DTG and DSC characterizations.

FIG. 3 shows exemplary DSC profiles of lyophilized silk powder with step heating. Heating rate is 10° C./min.

FIG. 4 shows exemplary DSC profiles of lyophilized silk powder. The solid line represents the standard DSC with heating rate of 2° C./min and the dotted line represents the temperature-modulated DSC (TMDSC) with a heating rate of 2° C./min. TMDSC uses a temperature amplitude of 0.318 K and a period of 1 min.

FIG. 5 shows a schematic illustration of the silk processing via heat and pressure. Process A (top row) shows a silk monolith obtained by heat pressing, then machined into silk screws. Process B (middle row) shows a silk screw obtained by direct molding of silk with heat and pressure. Process C (bottom row) shows a silk monolith obtained by heat pressing, then the monolith was molded into the shape of screw.

FIG. 6 panel (a) shows a schematic of the method combining top-down and bottom-up approaches to transform amorphous silk nanomaterials to bulk natural silk. Step 1, chemical treatment to dissolve natural silk fibers and make silk fibroin solution; step 2, freeze-drying treatment to make amorphous silk nanomaterials; step 3, mechanical hot-pressing at 632 MPa at variable temperatures, which leads to densification and structural transition of the silk fibroin. Panel (b) shows a schematic of silk fibroin's protein structure.

FIG. 7 panel (a) Shows photographs of silk bars, pins, plates, rods, tube and screw. A big silk plate was shown in panel (b) with a dimension of 4 cm (length)×2 cm (width). The scale bars are 1 cm.

FIG. 8 panel (a) shows photographs and cross-sectional SEM images of the bulk silk plates prepared at variable temperatures. The scale bars in A2-F2 and A3-F3 are 200 µm and 1 µm, respectively. Panel (b) shows an FTIR spectra of the bulk silk plates prepared at variable temperatures. Panel (c) shows an X-ray diffraction spectra of the bulk silk plates prepared at variable temperatures. Panel (d) shows β-sheet content of the bulk silk plates quantified from FTIR spectra analysis. Panel (e) shows crystallinity of the bulk silk plates estimated from X-ray diffraction spectra analysis. Panel (f) shows a schematic illustration showing a proposed mechanism of the structural transition of amorphous silk nanomaterials (ASN) during the thermal processing.

FIG. 9 panel (a) shows exemplary three-point bending curves for the silk plate prepared at variable temperatures. Panel (b) shows flexural strength and modulus of the silk plate prepared at variable temperatures. Panel (c) shows mechanical properties of natural materials compared to synthetic structural materials.

FIG. 10 shows a three-point bending test of silk plates prepared with different raw materials: degummed silk powder (black), amorphous silk nanomaterials (grey). The silk plates were prepared at 145° C. and 632 MPa. The flexural stress for silk plates prepared with degummed silk powder (45.9±9.1 MPa) is much lower than that prepared with amorphous silk nanomaterials (147.1±14.2 MPa).

FIG. 11 panel (a) shows density of silk plates prepared with different pressing temperatures. The density was calculated based on the measured mass, thickness and dimensions of the silk plates. Panel (b) shows a three-point bending test of silk plates prepared at 145° C. under different pressures (632 MPa and 125 MPa). The flexural stress for silk plates prepared with lower pressure is lower than that prepared with higher pressure.

FIG. 12 shows exemplary images of directly molded silk screw.

FIG. 13 panel (a) shows DSC curves of silk plate pressed at 125° C. and 632 MPa for 15 minutes. Panel (b) shows a silk screw obtained by molding a cylindrical silk monolith under heat and pressure. Panel (c) shows a photograph of silk structures made by thermal forming from silk plate pressed at 125° C. and 632 MPa for 15 minutes. Panel (d) shows images of the patterned silk dime coin. Panel (e) shows an SEM image of the nanostructure patterned silk film pattern nanostructures.

FIG. 14 shows a photograph and SEM images of machined silk screws (a, b, c) and ear tubes (d, e, f). The scale bars are 1 mm.

FIG. 15 shows degradation profiles of silk screws prepared at different temperatures (95° C., 125° C., 145° C.) in pure PBS (panel a), 5 U/mL Protease in PBS (panel b) and 40 U/mL Chymotrypsin in PBS (panel c). The corresponding SEM images of silk screws after 30-day degradation were present. The scale bars are 1 mm and 500 µm in upper and lower images respectively.

FIG. 16 shows a water uptake and swelling test (PBS, 37° C.) of silk screws by machining the silk bars prepared with different processing conditions (95° C. and 632 MPa; 125° C. and 632 MPa; 145° C. and 632 MPa).

FIG. 22 shows $^{13}C$ Chemical Shifts (in ppm from TMS) of Amino Acid Residues in liquid silk in *B. mori* gland, regenerated *B. mori* silk solution, degummed *B. mori* silk and lyophilized *B. mori* silk.

Figure 23:
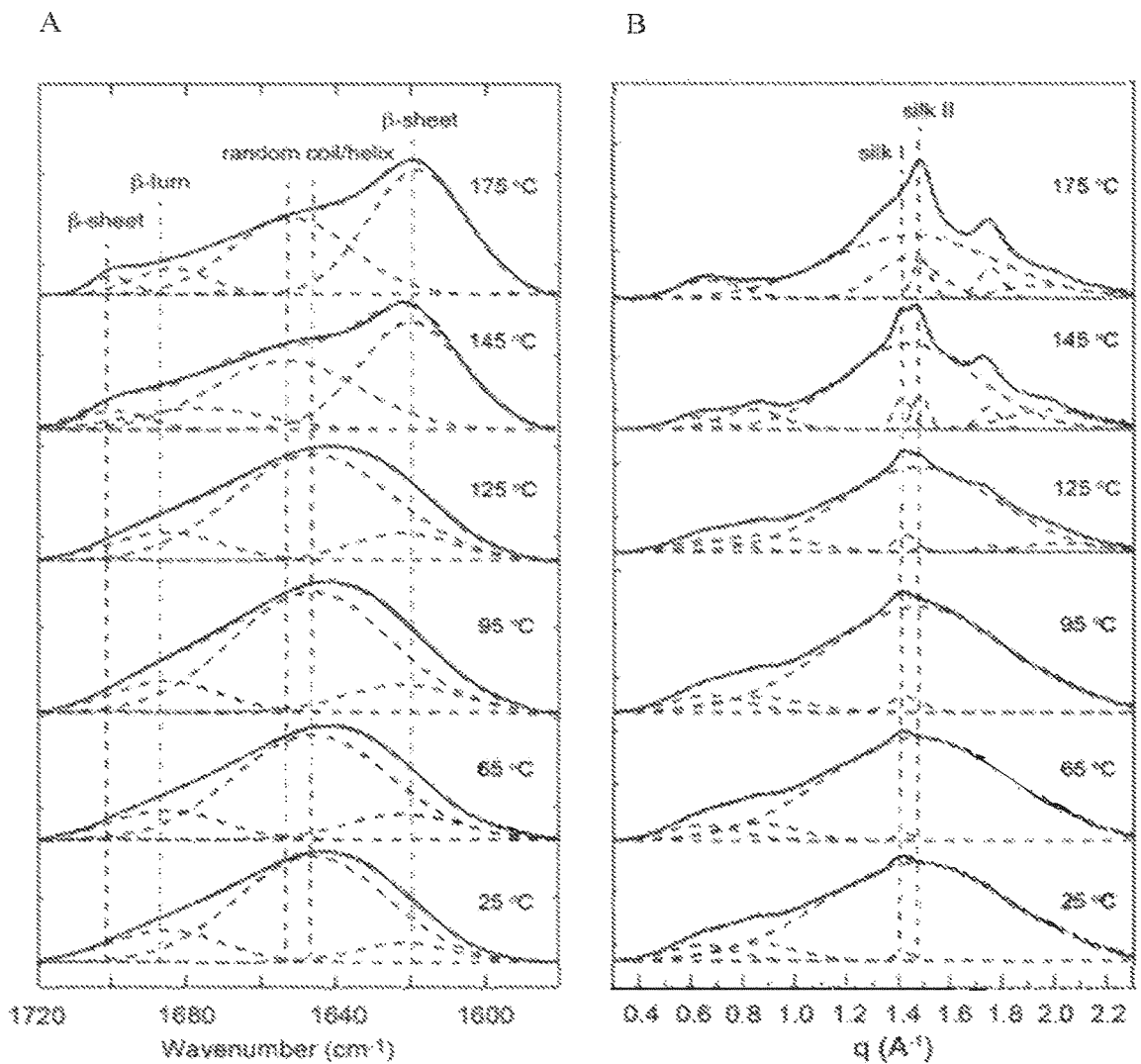

FIG. 23 shows deconvolution of amide I peak from FTIR spectra (panel A) and diffraction pattern from XRD (panel B). For FTIR spectra, the spectral corrections and decomposition were performed using a home-developed Matlab package. The spectra were first smoothed with a 5-point triangle smoothing method and then baseline corrected using a cubic spline for the amide I band. The deconvolution was carried out using a secondary derivative method with four primary peaks assigned to a variety of secondary structures respectively: 1620 cm$^{-1}$ (β-sheet), 1645-1655 cm$^{-1}$ (random coil/helix), 1685 cm$^{-1}$ (β-turn), and 1698 cm$^{-1}$ (β-sheet). For XRD, the 1D intensity profiles were fitted using multiple Gaussian peaks. The broad component at 1.48 A-1 represents the amorphous component.

Figure 24:
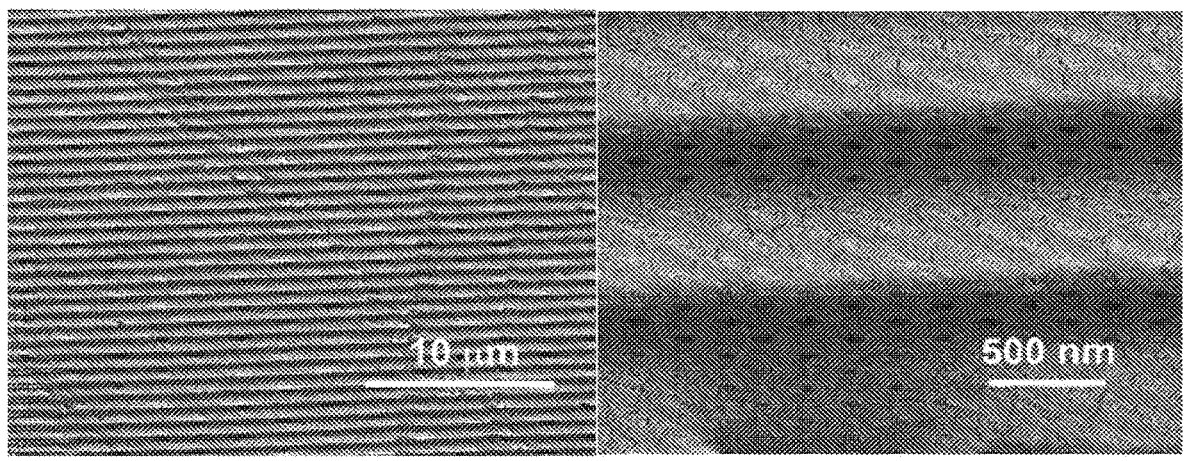

FIG. 24 shows SEM images of silk films imprinted with nanopatterns.

Figure 25:
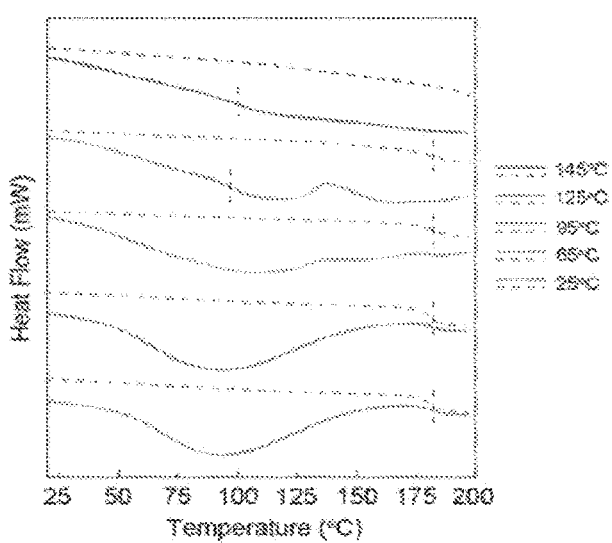

FIG. 25 shows standard DSC profiles for silk plates prepared at different temperatures. The samples were first heated from −50 to 200° C. with a heating rate of 10° C./min under a dry nitrogen gas flow of 50 mL/min. After cooling down to −50° C., the samples were heated back to 200° C. with a heating rate of 10° C./min. The first heating profiles were shown in solid lines and the second heating profiles were shown in dashed lines.

Figure 26A:
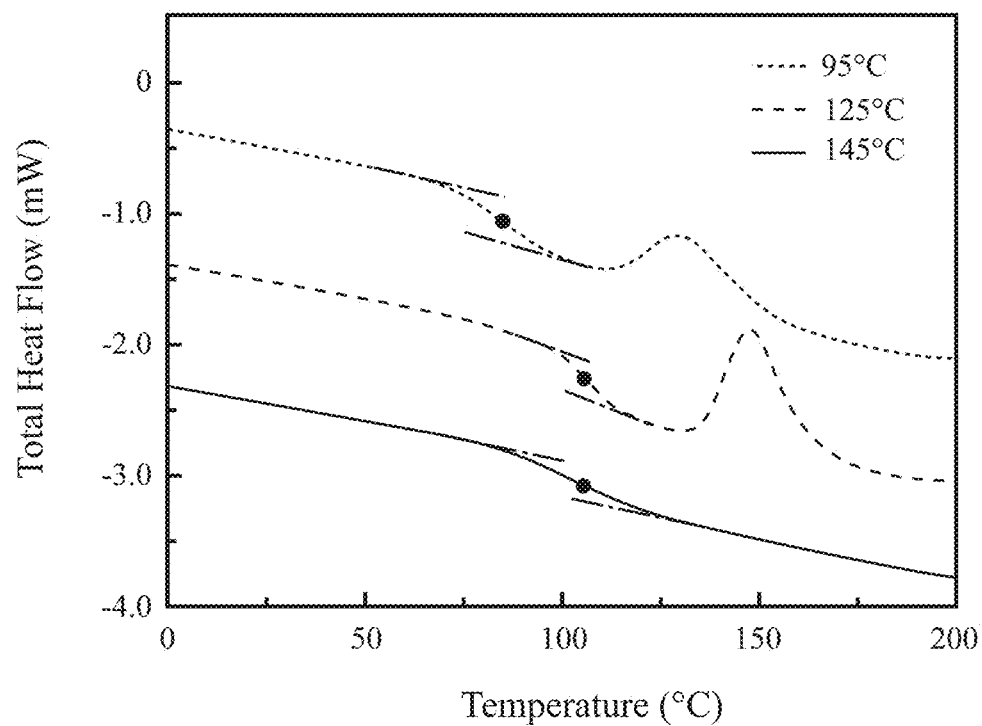
Figure 26B:
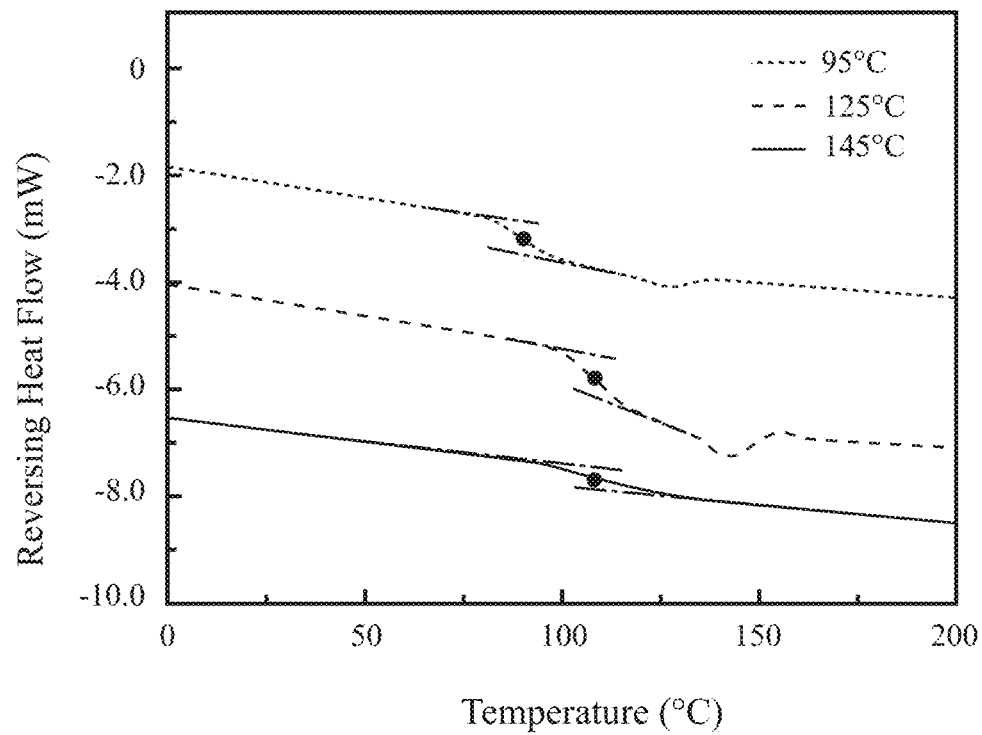

FIG. 26 shows exemplary temperature-modulated DSC (TMDSC) profiles for silk plates prepared at different temperatures (95° C., 125° C., 145° C.). The samples were heated from −50 to 200° C. with a heating rate of 10° C./min, a modulation period of 60 s and temperature amplitudes of 1.59° C. The total heat flow curves and reversing heat flow curves were shown in panel (A) and panel (B) respectively. The dashed tangent lines indicate the step change occurring at the glass transition temperature.

FIG. 27 is a table showing a comparison between different methods for fabricating silk monolith.

Figure 28:
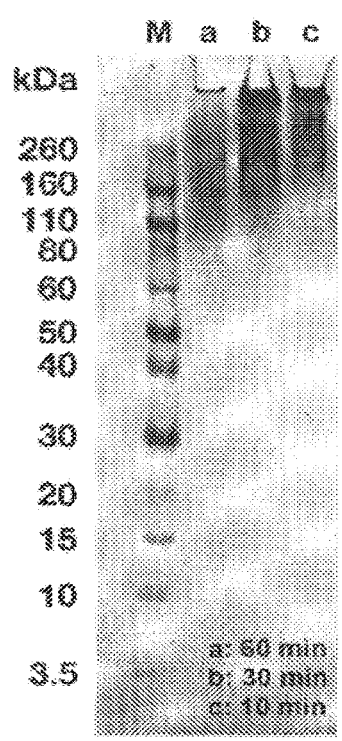

FIG. 28 shows the molecular weight distribution of silk fibroin in aqueous solution with different degumming times (10 min, 30 min, 60 min). Sodium dodecyl sulfate polyacrylamide gel electrophoresis (SDS-PAGE) was performed using 0.5 wt % silk solution. It shows that the averaged molecular weight of silk fibroin decreases with increasing degumming times. For degumming time of 30 min, the averaged molecular weight of silk fibroin is ~260 kDa.

FIG. 29 shows the complete protein sequence of *B. mori* silk fibroin.

Figure 30:
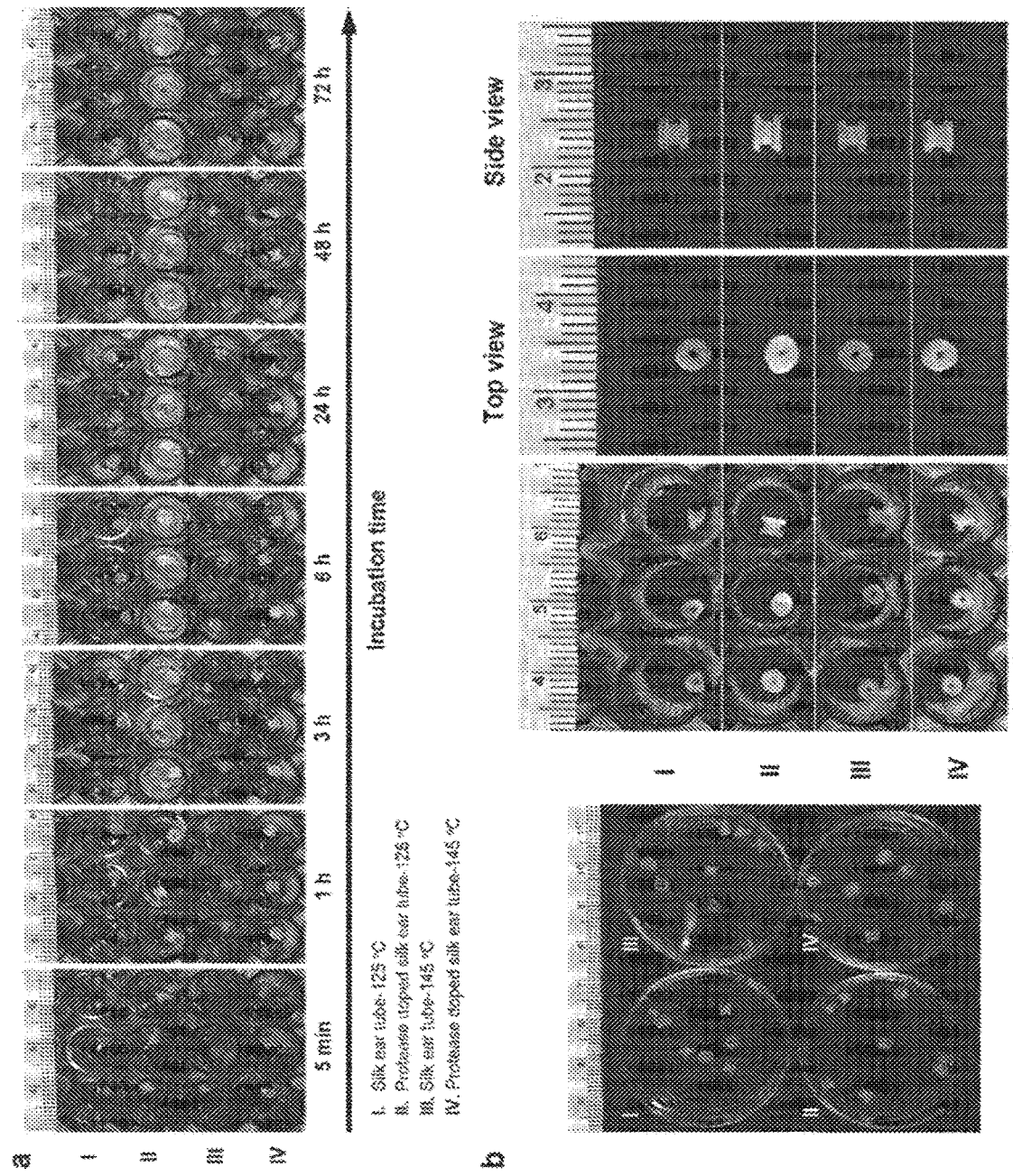

FIG. 30 shows in vitro degradation analysis of silk ear tubes with or without protease XIV doping: (a) photographs of silk ear tubes incubated in PBS at 37° C. for different times (5 min, 1 h, 3 h, 6 h, 24 h, 48 h and 72 h). The silk ear tubes were machined from pure silk or silk-protease XIV bulk materials prepared at two different conditions (125° C., 632 MPa; 145° C., 632 MPa). (b) Photographs of as fabricated silk ear tubes (left) and silk ear tubes after continuous incubation in PBS solution for 72 hours (right).

DETAILED DESCRIPTION

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" are used as equivalents and may be understood to permit standard variation as would be understood by those of ordinary skill in the art; and (v) where ranges are provided, endpoints are included.

Approximately: as used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biocompatible: the term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: as used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Compaction: as used herein, the term "compaction" refers to a process by which a material progressively loses its porosity due to the effects of loading.

Composition: as used herein, may be used to refer to a discrete physical entity that comprises one or more specified components. In general, unless otherwise specified, a composition may be of any form—e.g., gas, gel, liquid, solid, etc. In some embodiments, "composition" may refer to a combination of two or more entities for use in a single embodiment or as part of the same article. It is not required in all embodiments that the combination of entities result in physical admixture, that is, combination as separate co-entities of each of the components of the composition is possible; however many practitioners in the field may find it advantageous to prepare a composition that is an admixture of two or more of the ingredients in a pharmaceutically acceptable carrier, diluent, or excipient, making it possible to administer the component ingredients of the combination at the same time.

Fusion: as used herein, the term "fusion" refers to a process of combining two or more distinct entities into a new whole.

Hydrophilic: as used herein, the term "hydrophilic" and/or "polar" refers to a tendency to mix with, or dissolve easily in, water.

Hydrophobic: as used herein, the term "hydrophobic" and/or "non-polar", refers to a tendency to repel, not combine with, or an inability to dissolve easily in, water.

Improve, increase, or reduce: as used herein or grammatical equivalents thereof, indicate values that are relative to a baseline measurement, such as a measurement in a similar composition made according to previously known methods.

Macroparticle: as used herein, the term "macroparticle" refers to a particle having a diameter of at least 1 millimeter. In some embodiments, macroparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer. In some embodiments, a population of particles is considered a population of macroparticles if the mean diameter of the population is equal to or greater than 1 millimeter.

Microparticle: as used herein, the term "microparticle" refers to a particle having a diameter between 1 micrometer and 1 millimeter. In some embodiments, microparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer. In some embodiments, a population of particles is considered a population of microparticles if the mean diameter of the population is between 1 micrometer and 1 millimeter.

Nanoparticle: as used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer. In some embodiments, a population of particles is considered a population of nanoparticles if the mean diameter of the population is equal to or less than 1000 nm.

Physiological conditions: as used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Pure: as used herein, a material, additive, and/or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: as used herein describes a standard or control relative to which a comparison is performed. For example, in some embodiments, a material, article, additive, entity or other sample, sequence or value of interest is compared with a reference or control material, article, additive, entity or other sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Solid form: as is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized as a single such form (e.g., as a pure preparation of a single polymorph). In some embodiments, such entities may be utilized as a mixture of such forms.

Substantially: as used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Compositions and Methods

The present description encompasses, inter alia, the recognition that that application of one or more periods of each of elevated temperature and elevated pressure in particular ways cause previously unknown changes in the structure of silk fibroin, for example, in silk fibroin materials. In some embodiments, the present disclosure encompasses the surprising discovery that silk fibroin articles may be made directly from amorphous silk fibroin material, without the need for intermediate solubilization widely used in the art. Without wishing to be held to a particular theory, it is specifically contemplated that the new structures enabled by the methods disclosed herein result, at least part, from a combination of compaction and fusion of silk fibroin materials.

As a natural protein-based biopolymer, silk in various material formats has promising features including biocompatibility and biodegradability, along with outstanding mechanical properties. Accordingly, silk has been utilized as a material option for biomaterials and scaffolds in biomedical applications, including drug delivery, tissue engineering and regenerative medicine[1-4] for decades. Natural silk is a semi-crystalline biopolymer material, consisting of β-sheets nanocrystallites embedded in a less organized, less crystalline continuous phase due to the amphiphilic nature of the protein chemistry[5-7]. The strong hydrogen-bonding network in the β-sheets nanocrystallites contributes significantly to the stability and excellent mechanical properties of the silks, akin to cellulose, which challenges the ability to thermally process silk-based materials without degradation. In fact, there have only been limited reports of thermal melting and reconstitution of silk materials, which required ultrafast laser heating[8,9]. Further, historically, starting from Pauling's studies of the fundamental structural features of silk fibroin, the antiparallel β-pleated sheet (antiparallel β-sheet) that form the crystalline phase in silk is significantly stable due to the well aligned N—H—O hydrogen bonds[6,10].

Previously known methods of silk protein processing involve solution-based processing; as otherwise, the materials were often found to degrade prior to melting. During the past decades, researchers have made considerable effort in developing techniques to process silk fiber materials with an emphasis on extracting the silk fibroin from fibers and making silk solution. For instance, silk fibers after removing sericin on their exterior surfaces (degummed silk fibers) can be dissolved in aqueous LiBr/$CaCl_2$ solution with high salt concentrations to generate aqueous silk solution. In addition, degummed silk fibers are soluble in several organic solvents such as formic acid, trifluoroacetic acid, 1,1,1,3,3,3-hexafluoro-2-propanol (HFIP). These methods are aimed towards downstream processing (solvent removal) to generate silk materials, including gels, foams, films, new fiber formats and related materials[16-18]. Solvent addition and removal, with associated limits of solubility of the protein, lead to new and useful materials, but at a significant cost due to the various processing steps, along with limitations in material properties due to the limits in terms of solubility.

Prior to the present invention, methods using aqueous silk solution as starting materials were preferred since it is more human-friendly and it can be further used to make a variety of materials formats such as films, foams, sponges, hydrogels, tubes and bulk materials. However, the tendency of silk fibroin to self-assemble in aqueous solution makes the scale-up production and product quality control a challenging task. Moreover, besides the solution-based processing method, there are very limited established technologies for engineering and producing silk-based structural materials with tunable physical properties. To overcome the limitations and better process the silk materials, a simple and effective strategy to transform amorphous natural silk powder directly into a high-performance structural material with tunable mechanical properties is disclosed herein.

Figure 6A:
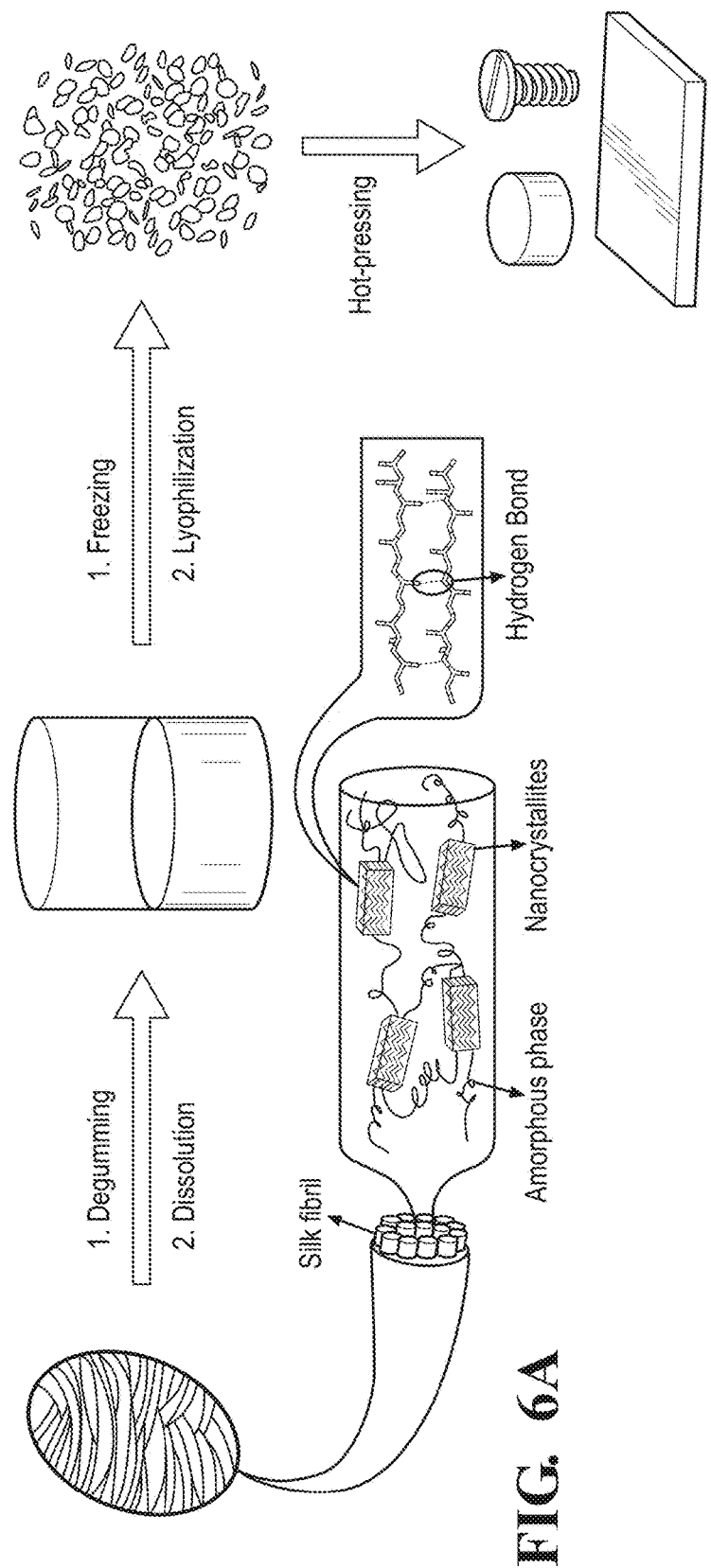
Figure 6B:
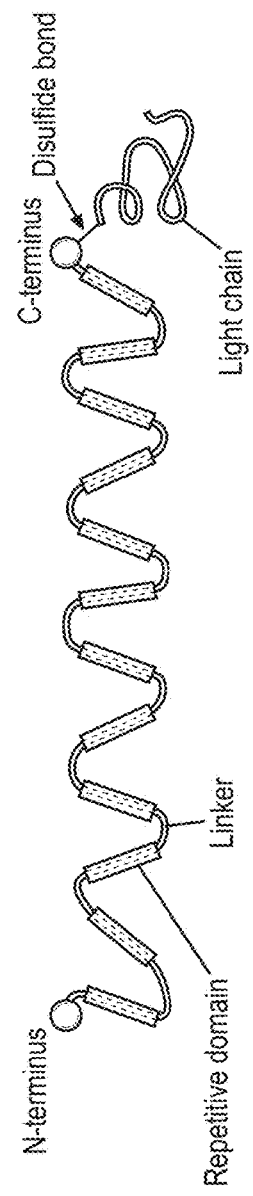

In some embodiments, methods disclosed herein involve the fabrication of amorphous silk nanomaterials (ASN) generated from aqueous silk fibroin solution. ASN may then be treated by hot pressing, leading to fusion and densification of the silk (e.g., into a silk article). The resulting silk bulk material exhibits specific strength higher than that of most natural structural materials and has been shown effective for fabricating silk-based composites. In addition, it is shown that the engineered silk material has thermoforming properties, which allows the materials to be further transformed to desirable shapes under proper conditions. FIG. 6 shows a schematic of certain provided methods combining top-down and bottom-up approaches to transform natural silk fibers into bulk silk parts. In some embodiments, compositions and methods described herein demonstrate a thermal and pressure-based, time-efficient and controllable method to transform silk fibroin from a silk fibroin material including substantial amounts of amorphous silk fibroin (for example, in powder form) directly to bulk structural materials. In some embodiments, methods and compositions described herein may allow for the application of more traditional process and molding techniques to silk materials, where this was not previously successfully employed for silk. Additionally, in some embodiments, processing methods described herein avoid the need for solvent or aqueous approaches, and providing direct routes to transform silk fibroin material into parts. In accordance with various embodiments, methods described herein provide for the transformation of silk fibroin from amorphous materials to a semi-crystalline high-performance structural material through controlled application of heat and pressure. In some embodiments, provided processes induce a conformation transition of silk molecules from random coil to β-sheet. In some embodiments, provided methods include the processing of natural silk fiber into amorphous silk material (e.g., powder) via degumming, silk fibroin solubilization and freeze drying to prepare the proper premolding materials; feeding the amorphous silk material into a predesigned mold; and inducing the conformation and structure change of silk by applying heat and pressure. Additionally, this method can be processed with silk alone, or with the addition of inorganic fillers or second polymers to generate composite devices.

With methods described herein using heat and pressure-assisted processing of amorphous silk precursor material, different formats of silk materials including plates, rods, screws, and tubes can be prepared with tunable mechanical properties and thermal forming property while retaining the good biocompatibility and degradability features of the materials. In some embodiments, methods described herein allow for green and cost-effective methods to transform natural fiber into silk monoliths compared to previous reported method (FIG. 27). This discovery completely alters the landscape in terms of silk-based materials processing methods, bringing more traditional process and molding techniques to silk materials where here-to-for this was not a method successfully employed for silk. The fabricated silk-based devices hold potential for a variety of biomedical applications, including implants for orthopedics. In addition, the heat and pressure assisted method can be extended to other protein-based materials (for example recombinant proteins) for fabricating protein-based monoliths.

In some cases, the methods described herein can include selecting an elevated temperature and an elevated pressure to produce a desired silk fiborni article of a desired crystallinity and desired material properties and then applying that elevated temperature and elevated pressure to a silk fibroin material having substantially amorphous structure. That is, the methods described herein can predictably select and apply temperatures and pressures to produce articles having desired crystallinity and material properties. This differs from other applications where heat and/or pressure can be applied to silk materials without a pre-determined desired outcome in terms of crystallinity and material properties.

The amount of plasticizer in the silk fibroin material can be adjusted to produce the desired crystallinity and material properties. This is particularly effective in low-temperature embodiments, where the amount of plasticizer is selected to produce the desired crystallinity and material properties. In some cases, the plasticizer is water.

Silk Materials

Any of a variety of silk materials may be used in accordance with various embodiments. In some embodiments, a silk material may be or comprise silk fibroin (e.g., degummed or substantially sericin free silk fibroin). In some embodiments, a silk material may be or comprise silk powder (e.g., comprising a plurality of silk particles).

In some embodiments, a silk fibroin material may be or comprise silk particles (e.g., microparticles or nanoparticles). As used herein, the term "particles" includes spheres, rods, shells, prisms, and related structures. While any application-appropriate particle size is contemplated as within the scope of the present disclosure, in some embodiments, a silk particle be have a diameter between 1 nm and 1,000 μm (e.g., between 1 nm and 1 μm, between 1 μm and 1,000 μm, etc). In some embodiments, a silk particle may have a diameter of greater than 1,000 μm.

Various methods of producing silk particles (e.g., nanoparticles and microparticles) are known in the art. For example, a milling machine (e.g., a Retsch planetary ball mill) can be used to produce silk powder. Generally, the ball mill consists of either two or four sample cups arranged around a central axis, which is geared such that each cup rotates both centrally and locally. Each ceramic cup is filled with small ceramic spheres. A range of sizes is available; balls with a diameter of 10 millimeters were/are used for the milling operations described in the present disclosure. As the cups spin, the spheres crush material in the cups to a small characteristic size. Both degummed and non-degummed silk can be converted from pulverized material to powder form in the ball mill.

In other embodiments, alternative powder formation techniques can be used (e.g., lyophilization or flash freezing and crushing). In other embodiments, alternative grates on the pulverizer, with larger holes, can be used. This can generate larger silk particle sizes.

In some embodiments, silk particles can be produced using a freeze-drying method as described in U.S. Provisional Application Ser. No. 61/719,146, filed Oct. 26, 2012, content of which is incorporated herein by reference in its entirety. Specifically, silk foam can be produced by freeze-drying a silk solution. The foam then can be reduced to particles. For example, a silk solution can be cooled to a temperature at which the liquid carrier transforms into a plurality of solid crystals or particles and removing at least some of the plurality of solid crystals or particles to leave a porous silk material (e.g., silk foam). After cooling, liquid carrier can be removed, at least partially, by sublimation, evaporation, and/or lyophilization. In some embodiments, the liquid carrier can be removed under reduced pressure. After formation, the silk fibroin foam can be subjected to grinding, cutting, crushing, or any combinations thereof to form silk particles. For example, the silk fibroin foam can be blended in a conventional blender or milled in a ball mill to form silk particles of desired size.

Figure 1:
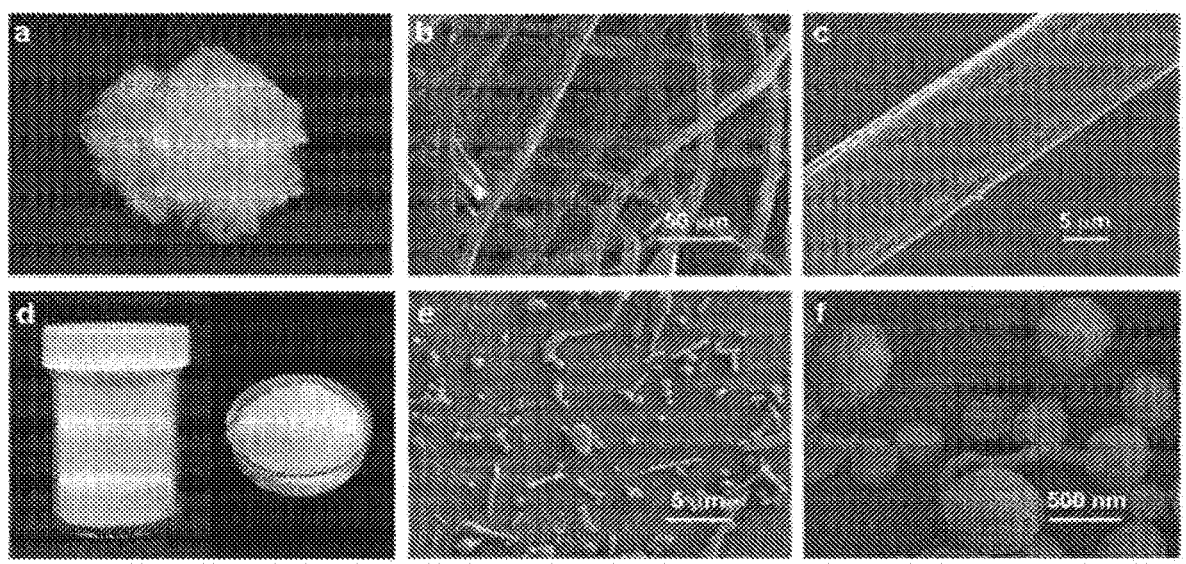
Figure 1G:
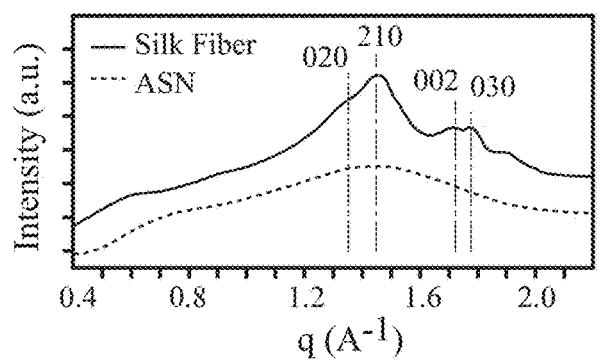
Figure 1H:
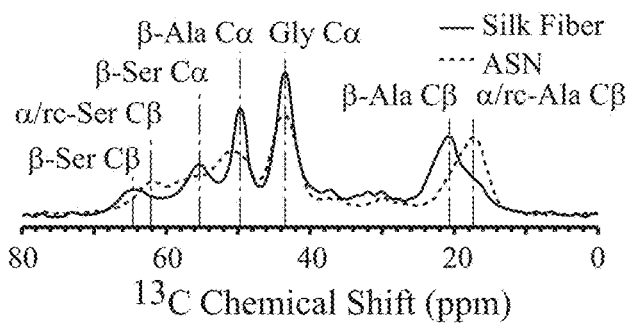
Figure 1I:
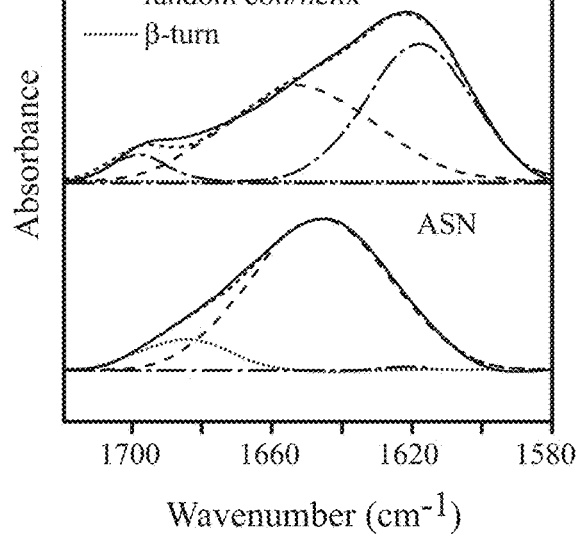
Figure 1J:
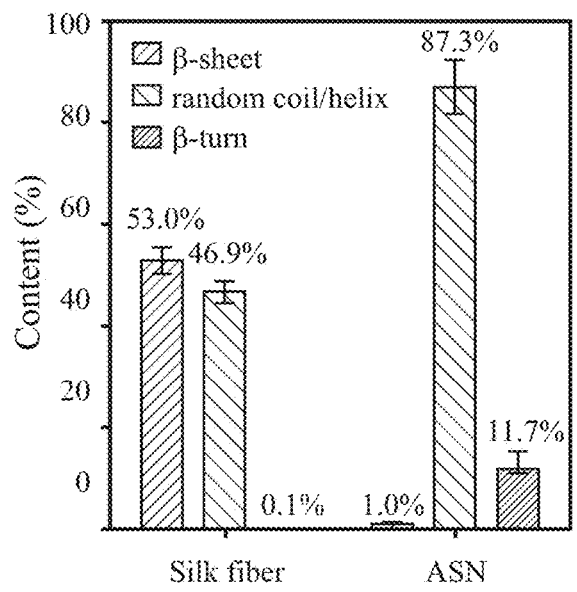

In some embodiments, the silk fibroin material comprising substantial amounts of amorphous structure is prepared from silk solution and is composed of nanostructures (as shown in FIG. 1), an may be referred to as nano-sized silk powder (NSP) and be part of materials referred to amorphous silk nanomaterials (ASN). As used herein, these terms are equivalent and may be used interchangeably.

Without wishing to be held to a particular theory, in some embodiments, the present disclosure encompasses the recognition that the use of particular starting materials (e.g., silk fibroin material comprising substantial amounts of amorphous structure) allows for the production of previously unattainable compositions. In some embodiments, a silk material is not made from solubilized silk. In some embodiments, a silk material may be lyophilized.

Silk Fibroin

According to various embodiments, any silk fibroin may be used in provided methods. In some embodiments, the silk fibroin is selected from the group consisting of spider silk (e.g., from *Nephila ciavipes*), silkworm silk (e.g., from *Bombyx mori*), and recombinant silks (e.g., produced/engineered from bacterial cells, yeast cells, mammalian cells, transgenic animals, and/or transgenic plants). In accordance with various embodiments, silk used in provided methods and compositions is degummed silk (i.e. silk fibroin with at least a portion of the native sericin removed). Degummed silk can be prepared by any conventional method known to one skilled in the art. For example, *B. mori* cocoons are boiled for a period of pre-determined time in an aqueous solution. Generally, longer degumming time generates lower molecular silk fibroin. In some embodiments, the silk cocoons are boiled for at least 60 minutes, at least 70 minutes, at least 80 minutes, at least 90 minutes, at least 100 minutes, at least 110 minutes, at least 120 minutes, or longer. Additionally or alternatively, in some embodiments, silk cocoons can be heated or boiled at an elevated temperature. For example, in some embodiments, silk cocoons can be heated or boiled at about 101.0° C., at about 101.5° C., at about 102.0° C., at about 102.5° C., at about 103.0° C., at about 103.5° C., at about 104.0° C., at about 104.5° C., at about 105.0° C., at about 105.5° C., at about 106.0° C., at about 106.5° C., at about 107.0° C., at about 107.5° C., at about 108.0° C., at about 108.5° C., at about 109.0° C., at about 109.5° C., at about 110.0° C., at about 110.5° C., at about 111.0° C., at about 111.5° C., at about 112.0° C., at about 112.5° C., at about 113.0° C., 113.5° C., at about 114.0° C., at about 114.5° C., at about 115.0° C., at about 115.5° C., at about 116.0° C., at about 116.5° C., at about 117.0° C., at about 117.5° C., at about 118.0° C., at about 118.5° C., at about 119.0° C., at about 119.5° C., at about 120.0° C., or higher. In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, the aqueous solution used in the process of degumming silk cocoons comprises about 0.02M $Na_2CO_3$. The cocoons are rinsed, for example, with water to extract the sericin proteins. The degummed silk can be dried and used for preparing silk powder. Alternatively, the extracted silk can dissolved in an aqueous salt solution. Salts useful for this purpose include lithium bromide, lithium thiocyanate, calcium nitrate or other chemicals capable of solubilizing silk. In some embodiments, the extracted silk can be dissolved in about 8M-12 M LiBr solution. The salt is consequently removed using, for example, dialysis.

In some embodiments, the silk fibroin is substantially depleted of its native sericin content (e.g., 5% (w/w) or less residual sericin in the final extracted silk). In some embodiments, the silk fibroin is entirely free of its native sericin content. As used herein, the term "entirely free" (i.e. "consisting of" terminology) means that within the detection range of the instrument or process being used, the substance cannot be detected or its presence cannot be confirmed. In some embodiments, the silk fibroin is essentially free of its native sericin content. As used herein, the term "essentially free" (or "consisting essentially of") means that only trace amounts of the substance can be detected, is present in an amount that is below detection, or is absent.

If necessary, a silk solution may be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk solution between about 10% to about 30%. In most cases dialysis for 2-12 hours can be sufficient. See, for example, International Patent Application Publication No. WO 2005/012606, the content of which is incorporated herein by reference in its entirety. Another method to generate a concentrated silk solution comprises drying a dilute silk solution (e.g., through evaporation or lyophilization). The dilute solution can be dried partially to reduce the volume thereby increasing the silk concentration. The dilute solution can be dried completely and then dissolving the dried silk fibroin in a smaller volume of solvent compared to that of the dilute silk solution. In some embodiments, a silk fibroin solution can optionally, at a suitable point, be filtered and/or centrifuged. For example, in some embodiments, a silk fibroin solution can optionally be filtered and/or centrifuged following the heating or boiling step. In some embodiments, a silk fibroin solution can optionally be filtered and/or centrifuged following the dialysis step. In some embodiments, a silk fibroin solution can optionally be filtered and/or centrifuged following the step of adjusting concentrations. In some embodiments, a silk fibroin solution can optionally be filtered and/or centrifuged following the step of reconstitution. In any of such embodiments, the filtration and/or centrifugation step(s) can be carried out to remove insoluble materials. In any of such embodiments, the filtration and/or centrifugation step(s) can be carried out to selectively enrich silk fibroin fragments of certain molecular weight(s).

In some embodiments, silk fibroin and/or a silk fibroin article, may comprise a protein structure that substantially includes β-turn and/or β-strand regions. Without wishing to be bound by a theory, the silk β sheet content can impact gel function and in vivo longevity of the composition. It is to be understood that composition including non-β sheet content (e.g., e-gels) can also be utilized. In some embodiments, silk fibroin has a protein structure including, e.g., about 5% β-turn and β-strand regions, about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of these embodiments, silk fibroin has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of these embodiments, silk fibroin has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions. In some embodiments, silk β sheet content, from less than 10% to ~55% can be used in the silk fibroin compositions disclosed herein.

In some embodiments, silk fibroin, or a silk fibroin article, has a protein structure that is substantially-free of α-helix and/or random coil regions. In aspects of these embodiments, the silk fibroin has a protein structure including, e.g., about 5% α-helix and/or random coil regions, about 10% α-helix and/or random coil regions, about 15% α-helix and/or random coil regions, about 20% α-helix and/or random coil regions, about 25% α-helix and/or random coil regions, about 30% α-helix and/or random coil regions, about 35% α-helix and/or random coil regions, about 40% α-helix and/or random coil regions, about 45% α-helix and/or random coil regions, or about 50% α-helix and/or random coil regions. In other aspects of these embodiments, the silk fibroin has a protein structure including, e.g., at most 5% α-helix and/or random coil regions, at most 10% α-helix and/or random coil regions, at most 15% α-helix and/or random coil regions, at most 20% α-helix and/or random coil regions, at most 25% α-helix and/or random coil regions, at most 30% α-helix and/or random coil regions, at most 35% α-helix and/or random coil regions, at most 40% α-helix and/or random coil regions, at most 45% α-helix and/or random coil regions, or at most 50% α-helix and/or random coil regions. In yet other aspects of these embodiments, the silk fibroin has a protein structure including, e.g., about 5% to about 10% α-helix and/or random coil regions, about 5% to about 15% α-helix and/or random coil regions, about 5% to about 20% α-helix and/or random coil regions, about 5% to about 25% α-helix and/or random coil regions, about 5% to about 30% α-helix and/or random coil regions, about 5% to about 40% α-helix and/or random coil regions, about 5% to about 50% α-helix and/or random coil regions, about 10% to about 20% α-helix and/or random coil regions, about 10% to about 30% α-helix and/or random coil regions, about 15% to about 25% α-helix and/or random coil regions, about 15% to about 30% α-helix and/or random coil regions, or about 15% to about 35% α-helix and/or random coil regions.

Elevated Temperatures

As discussed herein, provided methods and compositions include the exposure to elevated temperature(s). As used herein, the term "elevated temperatures" refers to temperatures higher than standard room temperature (i.e., greater than 25° C.). In some embodiments, provided methods or compositions include exposure to a single elevated temperature. In some embodiments, provided methods or compositions include exposure to at least two elevated temperatures (e.g., 3, 4, 5, 6, 7, 8, 9, 10 or more). In some embodiments where a method of composition includes two or more elevated temperatures, at least two of those elevated temperatures are different from one another.

In some embodiments, an elevated temperature may be between 25° C. and 200° C. By way of specific exemplary ranges, in some embodiments, an elevated temperature may be between 25° C. and 150° C., between 25° C. and 100° C., between 25° C. and 95° C., between 25° C. and 50° C., between 50° C. and 200° C., between 50° C. and 150° C., between 50° C. and 100° C., between 25° C. and 100° C. between 125° C. and 200° C., or any other range between 125° C. and 175° C.

In some embodiments, an elevated temperature may be at least 25° C. By way of additional example, in some embodiments, an elevated temperature may be at least 26° C., 27° C., 28° C., 29° C., 30° C., 35° C., 40° C., 45° C., 50° C., 55° C., 60° C., 65° C., 70° C., 75° C., 80° C., 85° C., 90° C., 95° C. or 100° C. In some embodiments, enhanced crystallization of silk fibroin material is observed at temperatures at or above 95° C.

In some embodiments, an elevated temperature may be at most 125° C. By way of additional example, in some embodiments, an elevated temperature may be at most 126° C., 127° C., 128° C., 129° C., 130° C., 135° C., 140° C., 145° C., 150° C., 155° C., 160° C., 165° C., 170° C., 175° C., 180° C., 185° C., 190° C., or 195° C.

Application of elevated temperature(s) to a provided composition or in a provided method may occur in any application-appropriate manner. By way of non-limiting example, in some embodiments, application of elevated temperature(s) may be via heat pressing, via a heating device such as an oven, heating stage, exposed flame or other mechanism.

Application of elevated temperature(s) may occur at or over any of a variety of time periods. For example, in some embodiments, application of elevated temperature(s) occurs substantially instantly (e.g., by placement over a flame or in an oven). In some embodiments, application of elevated temperature(s) occurs over a period of seconds, minutes, or hours. In some embodiments, application of elevated temperature(s) occurs over a period of time between 1 second and 1 hour.

Elevated Pressure

As discussed herein, provided methods and compositions include the exposure to elevated pressure(s). As used herein, the term "elevated pressures" refers to pressures higher than standard atmospheric pressure (i.e., 1.013 bar). In some embodiments, provided methods or compositions include exposure to a single elevated pressure. In some embodiments, provided methods or compositions include exposure to at least two elevated pressures (e.g., 3, 4, 5, 6, 7, 8, 9, 10 or more). In some embodiments where a method of composition includes two or more elevated pressures, at least two of those elevated pressures are different from one another.

Any application-appropriate method(s) may be used to cause elevated pressure as applied to provided compositions or in provided methods. By way of non-limiting example, in some embodiments, elevated pressure may include use of a vacuum, a press (e.g. heat press), and combinations thereof.

In some embodiments, application of elevated pressure may be or include uniaxial compression. In some embodiments, application of elevated pressure may be or include multi-axial compression (e.g., biaxial compression).

While any application-appropriate level of elevated pressure may be used, in some embodiments, an elevated pressure between 1 MPa and 1 GPa is used. By way of specific exemplary ranges, in some embodiments, an elevated pressure may be between 10 MPa and 1 GPa, between 50 MPa and 1 GPa, between 100 MPa and 1 GPa, between 200 MPa and 1 GPa, between 300 MPa and 1 GP, between 400 MPa and 1 GPa or between 500 MPa and 1 GPa. In some embodiments, an elevated pressure may be or comprise at least 1 MPa (e.g., at least 2 MPa, 3 MPa, 4 MPa, 5 MPa, 6 MPa, 7 MPa, 8 MPa, 9 MPa, 10 MPa, 20 MPa, 30 MPa, 40 MPa, 50 MPa, 60 MPa, 70 MPa, 80 MPa, 90 MPa, 100 MPa 150 MPa, 200 MPa, 250 MPa, 300 MPa, 350 MPa, 400 MPa, 450 MPa, 500 MPa, 550 MPa, 600 MPa, 650 MPa, 700 MPa, or 750 MPa).

Silk Articles

Provided methods and compositions allow for the production of previously unattainable silk articles, as well as silk articles with enhanced properties. In some embodiments, provided silk articles exhibit a substantially homogenous structure (e.g., as shown in FIG. 25, panel A). As used herein, "substantially homogenous structure" means that silk fibroin molecules are distributed and/or configured in a consistent way throughout substantially all of a portion of or the entirety of an article. Further, in some embodiments, silk articles may exhibit significant amounts of silk fibroin in a semi-crystalline structure (see e.g. FIG. 25, panel C and panel E). In some embodiments, production of a silk article according to provided methods includes a transition on the structure of silk fibroin from a substantially amorphous state to a semi-crystalline state, for example, as observed via X-ray diffraction.

In some embodiments, a silk article may exhibit significant amounts of β-sheet structure. For example, in some embodiments, a silk article may exhibit at least 10 wt % more (e.g., at least 20 wt %, 30 wt %, 40 wt %) β-sheet structures as compared to the starting silk fibroin material. In some embodiments, a silk article may exhibit at least 50 wt % more (e.g., at least 60 wt %, 70 wt %, 80 wt %, 90 wt %, 95 wt %) β-sheet structures as compared to the starting silk fibroin material.

In some embodiments, crystallinity of silk articles may be controlled by the application of temperature and pressure. For example, in some embodiments, when amorphous silk is processed at temperatures ranging from about 25° C.-125° C., the silk article may contain about 10-15% β-sheet structures. In some embodiments when amorphous silk is processed at temperatures ranging from about 125° C.-175° C., the silk article may contain for example, about 20-35% β-sheet structures or for example, over 40% β-sheet structures.

In some embodiments, provided methods and compositions allow for the production of silk articles which that are homogenous, where the silk amorphous powders are packed together via the bonding between neighboring raw silk powders, for example, at processing temperatures of about 25° C.-95° C. In some embodiments, provided methods and compositions allow for the production of silk articles which that are homogenous, where the silk molecules of amorphous powders gain more mobility as they are heated above the glass transition temperature and self-assemble into interlocked nanoglobules, for example, at processing temperatures of about 125° C.-175° C.

In some embodiments, provided methods and compositions allow for the production of silk articles (e.g., thin films) that undergo thermal softening and are bendable and moldable into a desired shape. In some embodiments, provided methods and compositions allow for the production of silk articles that are machinable.

Provided methods and compositions allow for the production of complex silk articles in ways that were not achievable using previous methods (e.g., silk screws that can resist torsion forces relevant to in vivo use). By way of non-limiting example, in some embodiments provided methods and compositions may be used to produce silk articles such as films, fibers, meshes, needles, tubes, plates, screws, rods, and any combination thereof.

In some embodiments, a silk article may be amenable to one or more types of patterning. In some embodiments, patterning may be or comprise macropatterning. In some embodiments, patterning may be or comprise micropatterning (i.e., patterning with micro scale features). In some embodiments, patterning may be or comprise nanopatterning (i.e., patterning with nano scale features). In some embodiments, patterning may be or comprise: etching, lithography-based patterning, carving, cutting, and any combination thereof.

In some embodiments, a silk article may be subjected to one or more types of processing (e.g., 2, 3, 4, 5, 6, 7, 8, 9, 10 or more). While any application-appropriate form of processing is contemplated as within the scope of the present disclosure, in some embodiments, processing may be or comprise machining, rolling, drilling, milling, sanding, punching die cutting, extruding, chemical etching, coating, molding, turning, thread rolling, and any combination thereof.

Exemplary Properties or Characteristics of Silk Articles

In some embodiments, provided compositions (e.g., silk articles) may be substantially transparent. In some embodiments, provided compositions (e.g., silk articles) may be semi-transparent. In some embodiments, provided compositions (e.g., silk articles) may be substantially non-transparent. As used herein, the term "transparent" refers to the propensity of an object to transmit light (with or without scattering of said light). In some embodiments, a composition/article is said to be substantially transparent if it transmits ≥80% of light it is exposed to in the visible range (400 nm-800 nm). In some embodiments, a composition/article is said to be semi-transparent if it transmits between 50%-80% of light it is exposed to in the visible range (400 nm-800 nm). In some embodiments, a composition/article is said to be substantially non-transparent if it transmits ≤50% of light it is exposed to in the visible range (400 nm-800 nm).

In some embodiments, provided compositions may be biocompatible and/or biodegradable. In some embodiments, provided compositions may exhibit particular degradation profile(s). By way of specific example, in some embodiments, a provided composition may degrade at least 50 wt % after about 96 hours of exposure to an aqueous environment at 37° C. In some embodiments, a provided composition may not degrade more than 10% after months of exposure to an in vivo environment or condition.

In some embodiments, provided compositions may exhibit one or more desirable properties including, but not limited to: electrical conductivity, enhanced machinability, and/or enhanced thermoformability.

Additives

In some embodiments, provided methods and compositions include one or more additives (e.g., 2, 3, 4, 5, 6, 7, 8, 9, 10 or more). In some embodiments, at least one additive may be mixed with or otherwise associated with a silk fibroin material prior to an applying step (e.g. exposure to one or more of elevated temperature and elevated pressure). In some embodiments, at least one additive may be mixed with or otherwise associated with a silk fibroin material substantially at the same time as an applying step). In some embodiments, at least one additive may be mixed with or otherwise associated with a silk fibroin material subsequently to an applying step.

Provided methods and compositions are amenable to the addition of any of a variety of additives. By way of non-limiting example, in some embodiments an additive may be or comprise a small molecule, an organic macromolecule, an inorganic macromolecule, an electrically conductive material, an inorganic material, a hydrophobic material, a hydrophilic material, a nanomaterial, and any combination thereof.

The processing of the silk-based materials, including pure silk materials and silk-based composite materials, can be modified with addition of one or more additives. In some embodiments, a function of an additive may be to tune the processing conditions and the properties of the products. In some embodiments, additives may be selected from water; glycerol; saccharides; biological macromolecules, e.g. peptide, proteins; antibodies and antigen binding fragments; nucleic acids; immunogens; antigens; enzyme; synthetic polymers, e. g. poly(ethylene) glycol, poly-lactic acid, poly (lactic-co-glycolic acid) to name but a few specific examples, though any application-appropriate additive is specifically contemplated as within the scope of the present disclosure.

In some embodiments, for example some embodiments contemplated for in vivo use, provided compositions may comprise one or more proteases. In some embodiments, an organic macromolecule is or comprises at least one protease. In some embodiments, a protease is or comprises one or more of Proteinase XIV, Proteinase K, a-chymotrypsin, collagenase, matrix metalloproteinase-1 (MMP-1), and MMP-2. In some embodiments, a protease may be useful in tailoring the degradation profile of a particular provided composition (e.g., in an in vivo environment).

In some embodiments, an electrically conductive material may be or comprise an organic conductive material and/or an inorganic conductive material (e.g., a metal). In some embodiments, an electrically conductive material may be or comprise at least one of a conductive polymer, graphene, silver, gold, aluminum, copper, platinum, steel, brass, bronze, and iron oxide.

Any application-appropriate amount of one or more additives may be useful according to various embodiments. By way of non-limiting example, in some embodiments, an additive may be present in a provided composition in an amount between 0.001 wt % and 95 wt %. In some embodiments, one or more additives may be mixed with a silk fibroin material in an amount ranging between 0.001 wt % and 95 wt % of the silk fibroin material.

EXAMPLES

Example 1—Preparation of Aqueous Silk Solutions for the Production of Lyophilized Silk Aqueous silk solution was prepared by dissolving degummed silk fibers (silk fibers after removing sericin on their exterior surfaces) in aqueous LiBr/CaCl$_2$ solution with high salt concentrations to generate aqueous silk solution. *Bombyx mori* (*B. mori*) cocoons were cut into small pieces and boiled in an aqueous 0.02 M Na$_2$CO$_3$ solution (Sigma-Aldrich, USA) for 30 min, followed by rinsing in distilled water to remove the Na$_2$CO$_3$ and sericin. The degummed silk was allowed to dry at room temperature for overnight. Then 20 grams of dried degummed silk was dissolved in 100 mL of 9.3 M LiBr solution at 60° C. for 3-4 h. The solution was subsequently dialyzed for 3 days in distilled water using Slide-a-Lyzer dialysis cassettes (MWCO 3,500, Pierce, USA). The water was changed five times during the dialysis (1 h, 4 h, 8 h, 24 h, 48 h). After dialysis, the solution was centrifuged for 10 min at 13,000 rpm to remove insoluble impurities. The concentration of the final silk solution was determined by drying a known volume of solution and measuring the mass of the remaining solid (~6 w/v %).

Example 2—Characterization of Amorphous Silk Material

Natural silk fibers from silkworm cocoons (*Bombyx mori*) comprise silk fibroin, a native protein with a ~390 kDa heavy chain and a ~25 kDa light chain[5,19]. Aqueous silk solution is obtained by breaking the hydrogen-bond network in degummed natural silk fibers with concentrated salt solutions to form regenerated silk solution. The fresh silk solution is then further diluted and freeze-dried to obtain amorphous silk materials (FIG. 1, panel D, panel E, panel F) in solid state, which is more stable than silk solution and can be stored at ambient condition without significant structural change for years.

In this Example, fresh solubilized silk is lyophilized and then further processed into particles, then molded through heat and compression in order to form different final structures. In order to understand the properties of the final material, the properties of the starting material were evaluated and compared with the material properties of native silk.

Fresh solubilized silk can be transformed back to solid silk format via freeze-drying to produce lyophilized silk. Here, it was found that the lyophilized silk has very similar fibroin structures (predominantly random coil) to that in solution state. More significantly, dried lyophilized silk can be stored under ambient condition for years without noticeable structure change. Compared to raw silk cocoon fibers and degummed silk fibers, lyophilized silk lacks well-defined hierarchical structure composed of secondary structures (e.g., β-sheets). It is an amorphous material with random coil structures. Due to such significant structural difference, the thermal or mechanical behavior of lyophilized silk differs from those for raw silk cocoon fibers and degummed silk fibers.

Figure 2A:
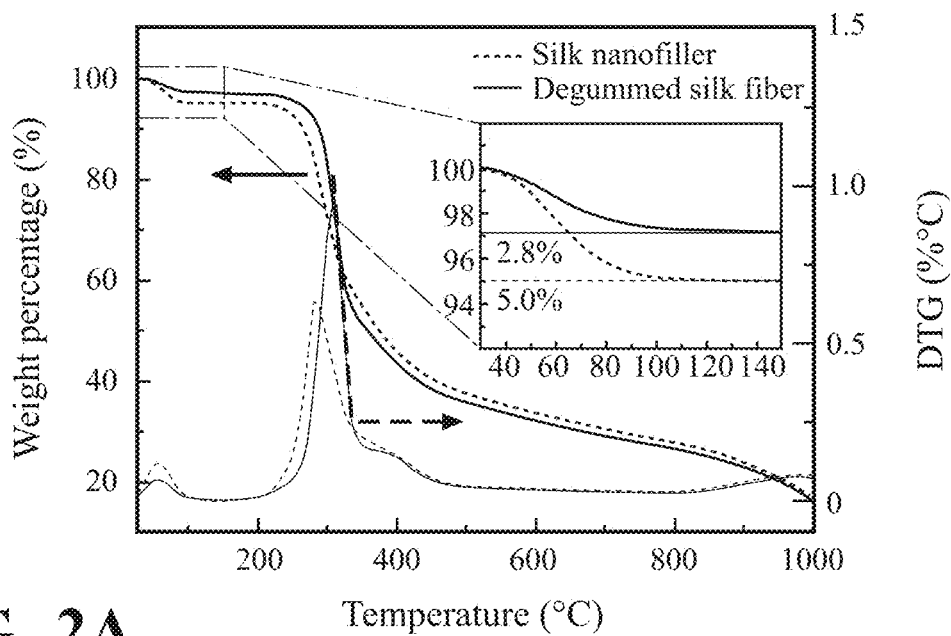
Figure 2B:
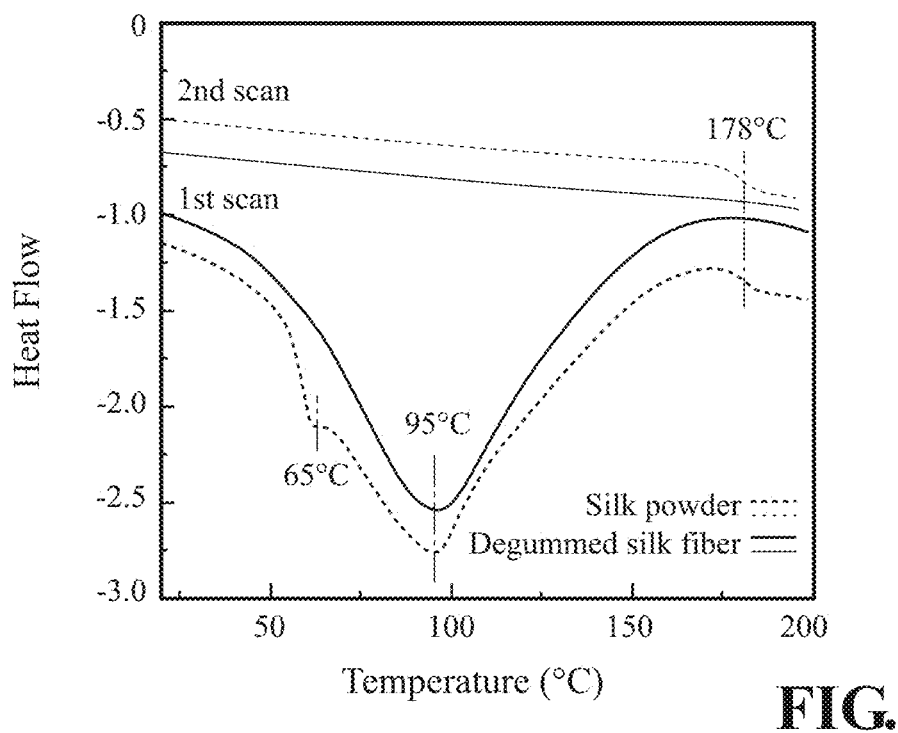

FIG. 2 panel (A) shows the thermal properties of the degummed silk fiber and lyophilized silk powder. From thermal gravimetric analysis (TGA), lyophilized silk had higher water content (5.0 wt %) than degummed silk fiber (2.8 wt %).

Differential scanning calorimetry (DSC) characterization further indicates that lyophilized silk had a water-associated glass transition around 65° C. and a glass transition of pure silk fibroin at 178° C., which are not found in degummed silk fibers (FIG. 2 panel B).

Figure 3:
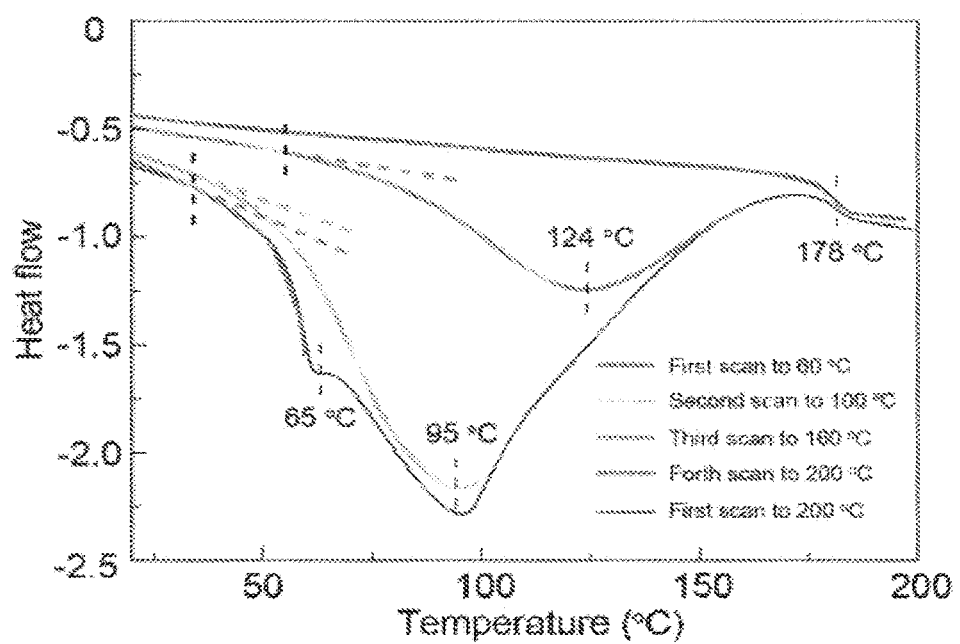

A more detailed DSC study on lyophilized silk was carried out in order to understand the structure change during the heating and the result was present in FIG. 3. During heating, silk-water system undergoes a dynamic conformation and composition change with a combination of the silk fibroin chain reorganization and the evaporation of the bound water. Specifically, silk fibroin may first reorganize to form a new conformation with the bound water as a plasticizer, which was demonstrated at a low temperature range (35° C.-80° C.). A well-resolved glass transition of the silk-water system was shown at 65° C. As the silk is further heated, bound water molecules start to release simultaneously. Two types of bound water molecules were found in the system which include weakly bound and strongly bound water molecules. Weakly bound water molecules started evaporating around 35° C. with a maximum evaporation rate at 95° C., while the strongly bound water molecules started evaporating around 55° C. with a maximum evaporation rate at 125° C. When temperature reached 160° C., all of the bound water molecules were evaporated. With contiguously heating, a stable glass transition of the pure silk fibroin was shown to be around 178° C. The heating rate is 10° C./min for TGA, DTG and DSC characterizations.

DSC measurements were carried out under a dry nitrogen gas flow of 50 mL/min with samples encapsulated in aluminum pans. In standard DSC measurements, the samples were heated from −50 to 200° C. with a heating rate of 10° C./min. The water content of ASN is similar to reported value for solution cast silk fibroin with less ordered structures[27,28].

Figure 4:
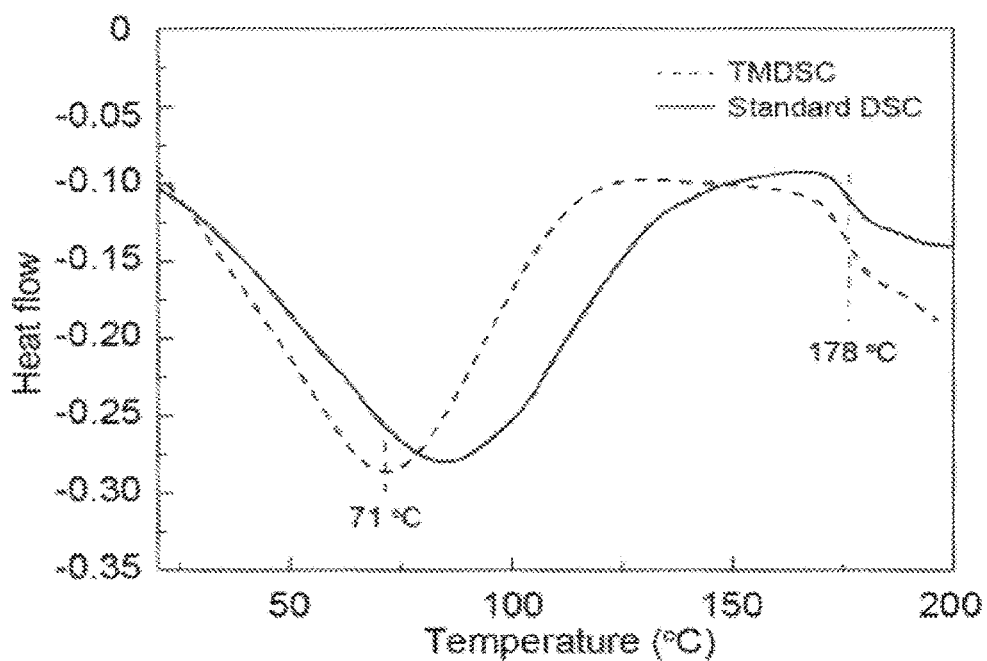

Thermal analysis showed that ASN had a water content of 5.0±0.5 wt % (FIG. 2, panel A) significantly higher than degummed native silk fibers (·2.8±0.3 wt %). Differential scanning calorimetry (DSC) showed that ASN had a water-associated glass transition at 65° C. and a stable glass transition temperature at 178° C. (FIG. 2, panel B), which agrees well with previous study on amorphous silk films (see Hu, X., Kaplan, D. & Cebe, P. Determining Beta-Sheet Crystallinity in Fibrous Proteins by Thermal Analysis and Infrared Spectroscopy. *Macromolecules* 39, 6161-6170 (2006)). A detailed stepwise scanning profile further indicated two types of bound water with amorphous silk material, weakly bound with a maximum evaporation rate at 95° C., and strongly bound water with a maximum evaporation rate at 125° C. (FIG. 2, panel C). Differential scanning calorimetry (DSC) characterization further indicates that lyophilized silk has a water-associated glass transition around 71° C. (from TMDSC) and a glass transition of pure silk fibroin at 178° C., which are not found in degummed silk fibers (FIG. 4). In this example, the silk fibroin showed a well-resolved glass transition of the silk-water system at 71° C. With contiguous heating, a stable glass transition of the pure silk fibroin was observed around 178° C. The heating rate was 2° C./min, a temperature amplitude of 0.318 K and a period of 1 min.

X-ray diffraction (XRD), Fourier transform Infrared spectroscopy (FTIR) and solid-state NMR spectroscopy showed that the silk fibroin in amorphous silk materials was primarily amorphous in structure, with a low content (~1.0%) of β-sheet structures (FIG. 1, panel G, panel H, panel I, panel J).

Example 3—Engineering Silk Monolith with Amorphous Silk Materials at Various Temperatures and High Pressure Natural silk fibers possess a very stable molecular structure containing strong hydrogen bonding networks at ambient and high pressure conditions[26], which limits the direct thermal processing of raw silk fibers. By reconstitution of natural silk into amorphous silk, the molecular structure of silk fibroin becomes less ordered. At high pressure and elevated temperature, the free-energy change of the materials system (Gibbs free energy G=E+PV−TS) may allow new opportunities to tune phases or molecular structure of the material, which inspired us to investigate how external pressure (or stress) and heat influence silk protein assembly in the solid state.

The amorphous silk is obtained via freeze-drying and used as raw materials in densification and thermal processing. A combination of molecular structural (XRD, FTIR) and morphological analysis (SEM) reveals that increasing the processing temperature during densification facilitates the self-assembly of amorphous silk fibroin. The pressure-driven densification of raw ASN may promote the intermolecular interaction, including hydrogen-bonding and van der waals interactions, which accounts for the formation of new β-sheet structures.

Figure 5:
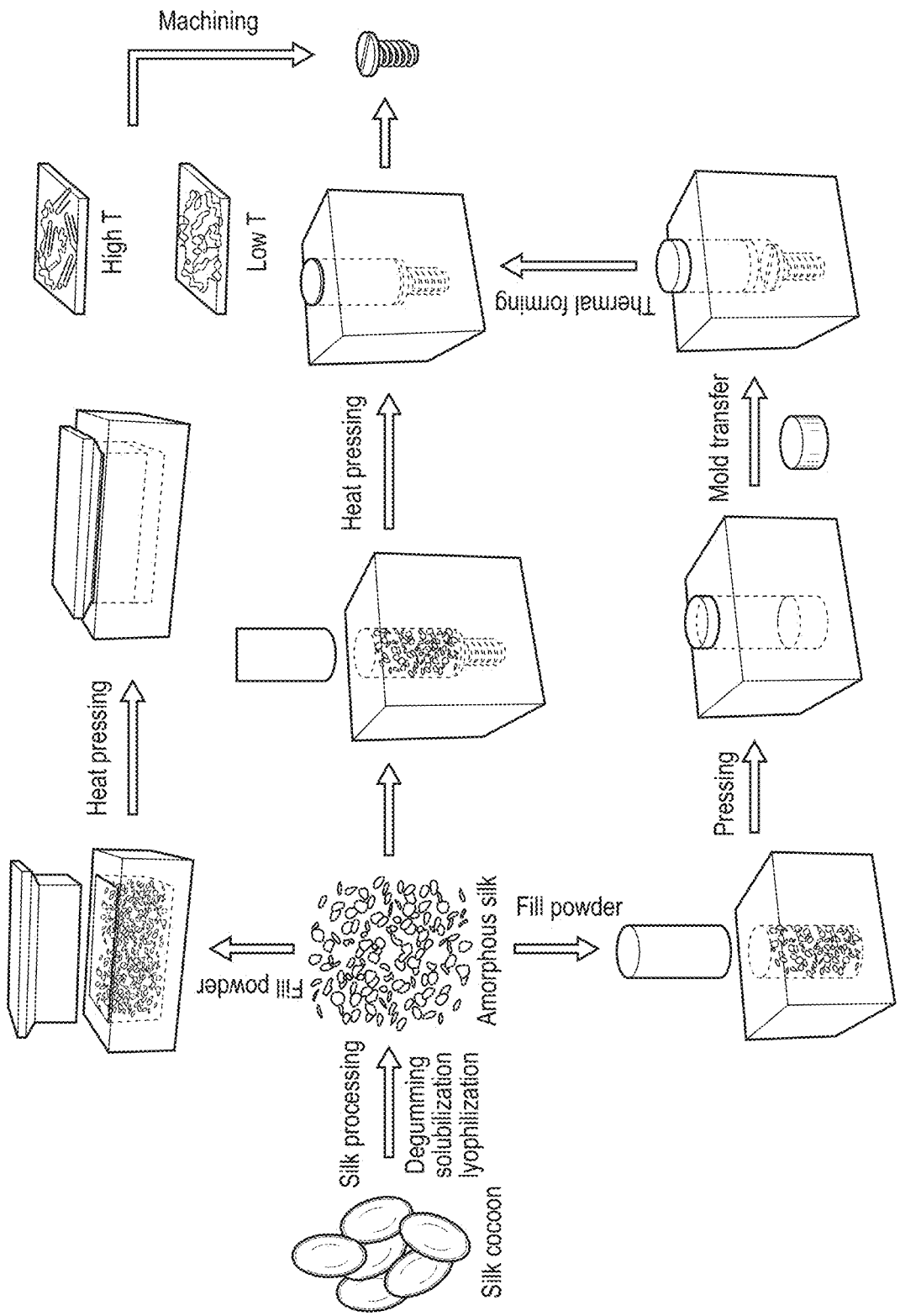
Figure 7:
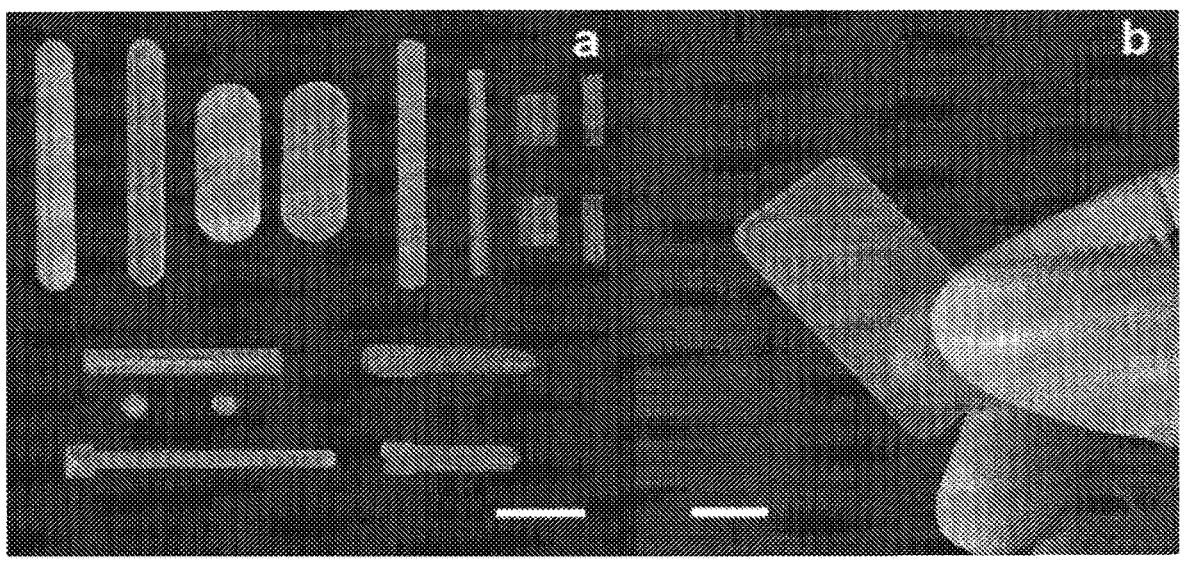

Regenerated amorphous silk prepared from silk solution of various concentrations (<7 wt %) were used as raw materials for the fabrication of silk materials via the heat/pressure process. In this example, regenerated amorphous silk powders prepared from 1% silk solution were used as exemplary starting materials for the production of silk materials in a variety of formats. In this example, the effect of heat and pressure on silk structure was further examined and further demonstration various processing routes to engineer amorphous silk material into functional devices (e.g. silk screw) with heat and pressure (FIG. 5). A collection of silk parts fabricated via different processing routes is shown in FIG. 7.

The method used for engineering and inducing the structure change of ASN is controlled application of pressure and heat. The applied pressure ranges from 1 MPa to over 1 GPa and temperature ranges from 0° C. to 200° C. The temperature is controlled lower than 200° C. as the silk fibroin starts degrading around 200° C. ASN were filled into pre-designed mold and compacted into silk plates at various temperatures at 632 MPa. As the temperature increases, the silk plate shows from opaque to transparent to yellow pale in appearance. Scanning electron microcopy analysis showed a striking difference between the inner structure of silk plates processed at low (25, 65 and 95° C.) and high temperatures (125, 145 and 175° C.). At low processing temperatures, despite the denser packing density and greater plastic deformation of raw silk powder with increased temperature, features similar to the dimension of the raw silk powder still exist (FIG. 8 panel a: A2-C2, and A3-C3). Silk globules of ~30 nm were observed at high processing temperatures (FIG. 8 panel a: D3-F3), which is similar to the globular structures in the natural silkworm and spider silk fibers.

Figure 8A:
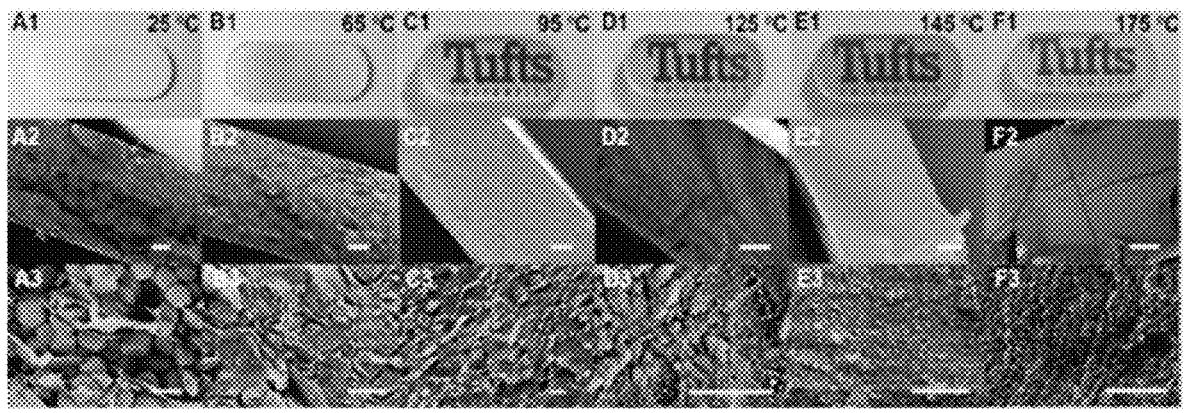
Figure 8B:
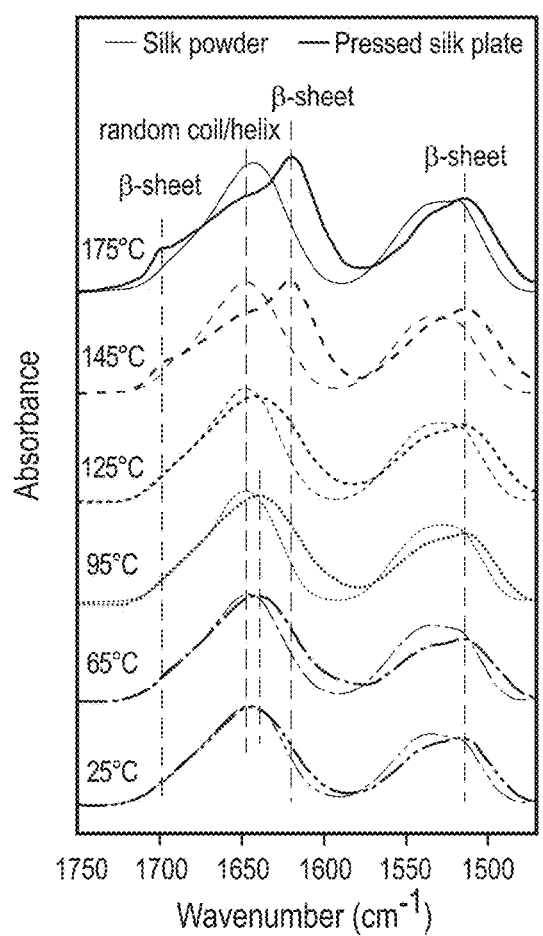
Figure 8C:
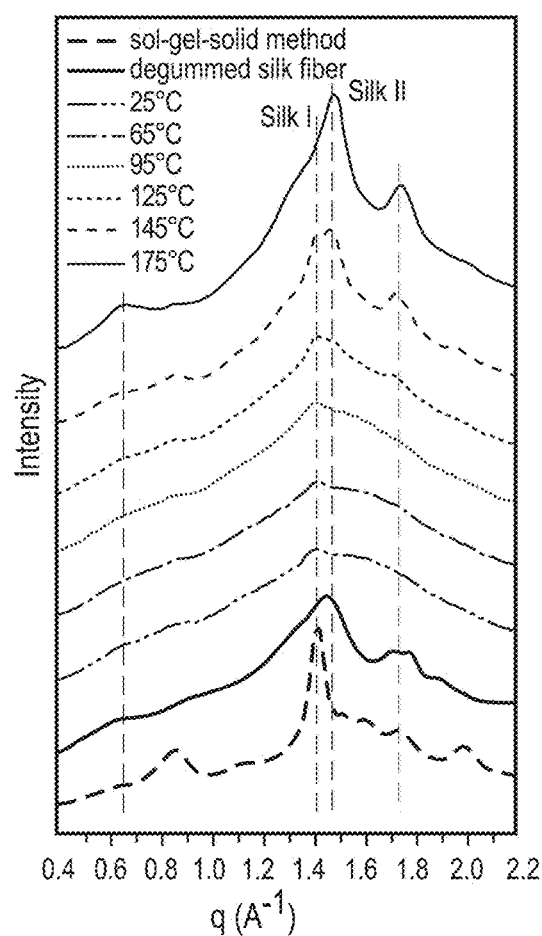

The Fourier-transform infrared spectroscopy (FTIR) analysis showed that a small amount of β-sheet structures (~10-15%) formed at low processing temperatures (25° C., 65° C., 95° C., 125° C.), and a higher amount of β-sheet structures formed (over 40%) at high processing temperature (145° C., 175° C.) (FIG. 8, panel B and panel D). In addition, X-ray diffraction (XRD) characterization shows that the crystallinity of the densified silk plates increases slowly with elevating temperatures in the temperature range from 25 to 95° C. By contrast, the crystallinity increases drastically with temperature when the hot pressing was performed over 125° C. (FIG. 8, panel C and panel E). At low temperatures (25, 65 and 95 □C), silk amorphous powders may be packed together via the bonding between neighboring particles with the formation of low content of β-sheet structure; at high temperatures (125, 145 and 175 □C), silk molecules may gain more mobility above the glass transition temperature and self-assemble into structures characteristic of interlocked nanoglobules and moderate crystallinity (~20-35%). In addition, XRD revealed silk II structure (as in native silk fibers) when the hot pressing was performed at >95° C., indicating a structural transition (from silk I to silk II) during the processing (FIG. 8, panel C). A brief mechanism was proposed to show the structural transition of ASN during the thermal processing (FIG. 8, panel F).

Figure 9A:
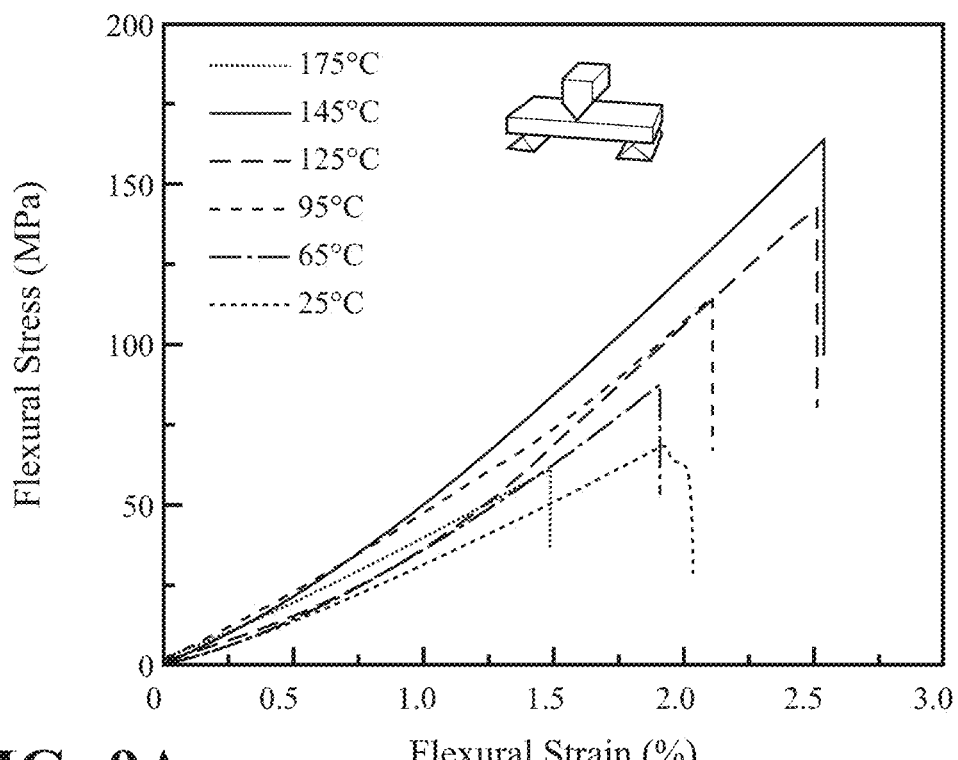
Figure 9B:
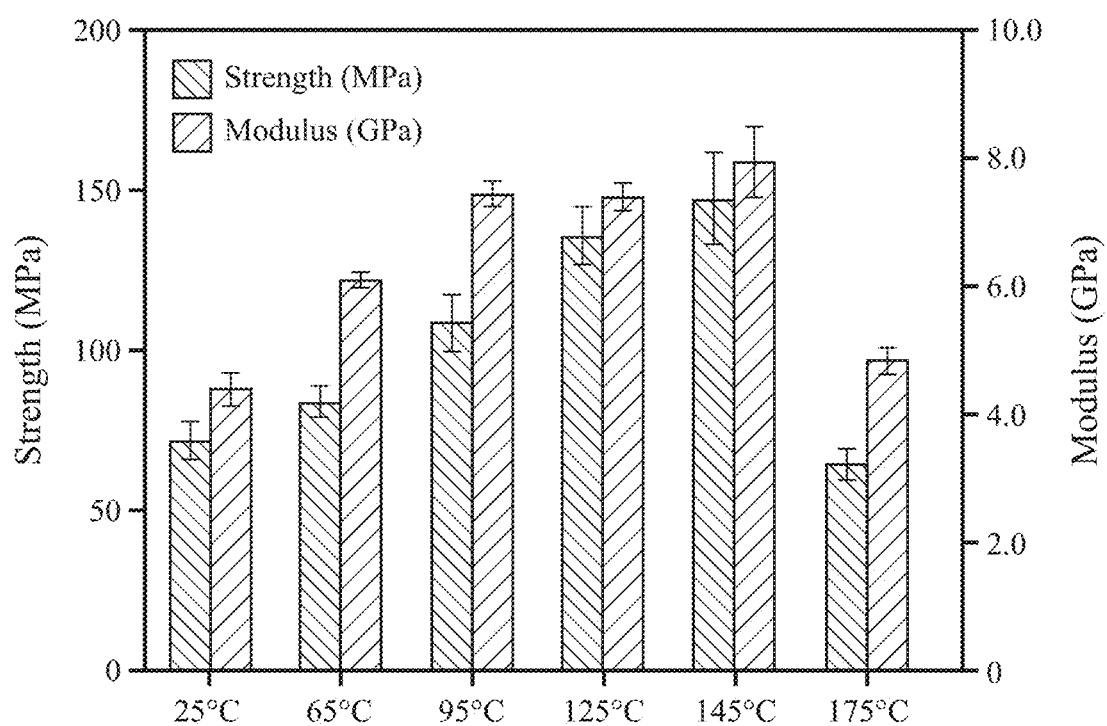
Figure 9C:
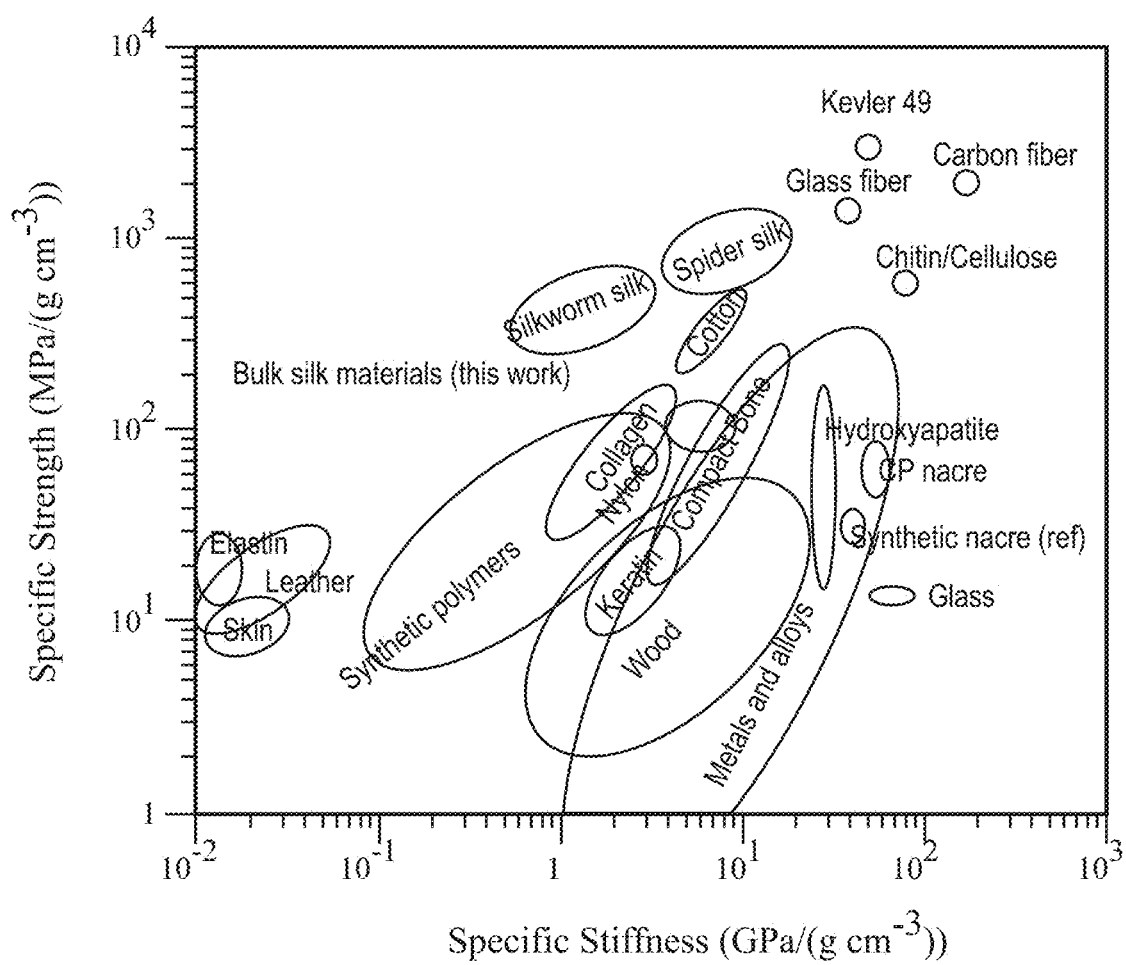
Figure 10:
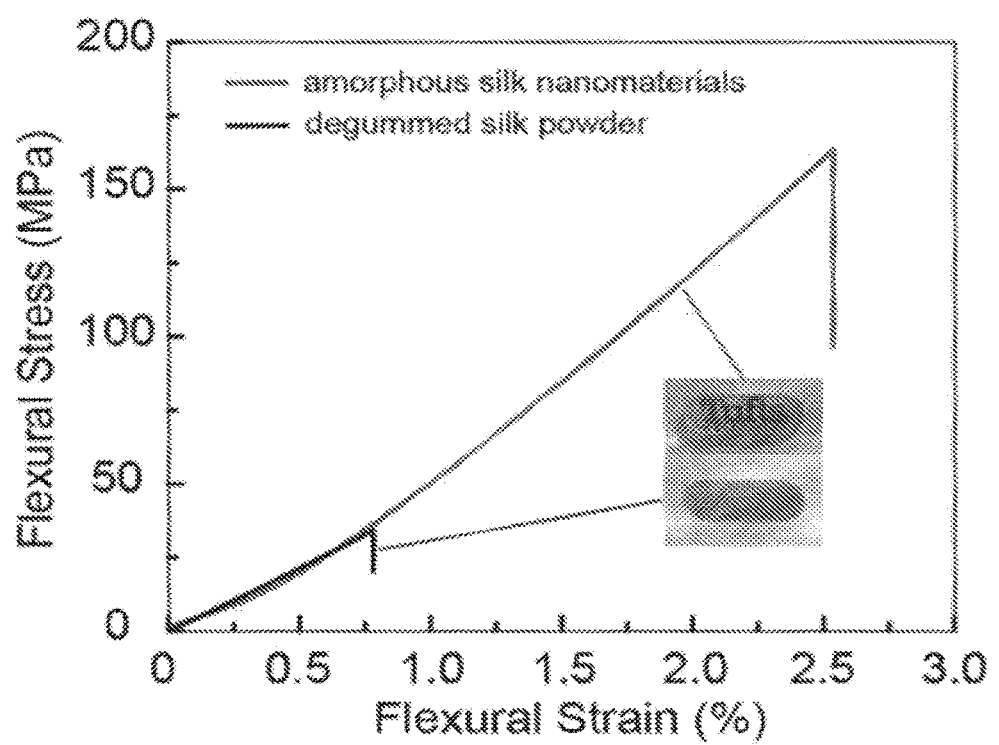

In one example, the mechanical properties of the thermal processed bulk silk materials were characterized with three-point bending test. With increased processing temperature (25° C.-145° C.), the strength of the bulk silk materials increased (FIG. 9, panel A and panel B), however, at 175° C., strength starts to decrease, which may be due to the high crystallinity and partial thermal degradation. The maximum strength was achieved for the silk plates processed at 145° C. with a specific strength of 109±10 MPa/g cm$^{-3}$, which exceeds those of some natural structural materials such as CP nacre and wood (FIG. 9, panel C). In contrast, the densification of degummed silk powder of high β-sheet content and crystallinity shows inferior mechanical properties, which may indicate weaker fusion of the degummed silk powder (FIG. 10).

Figure 11:
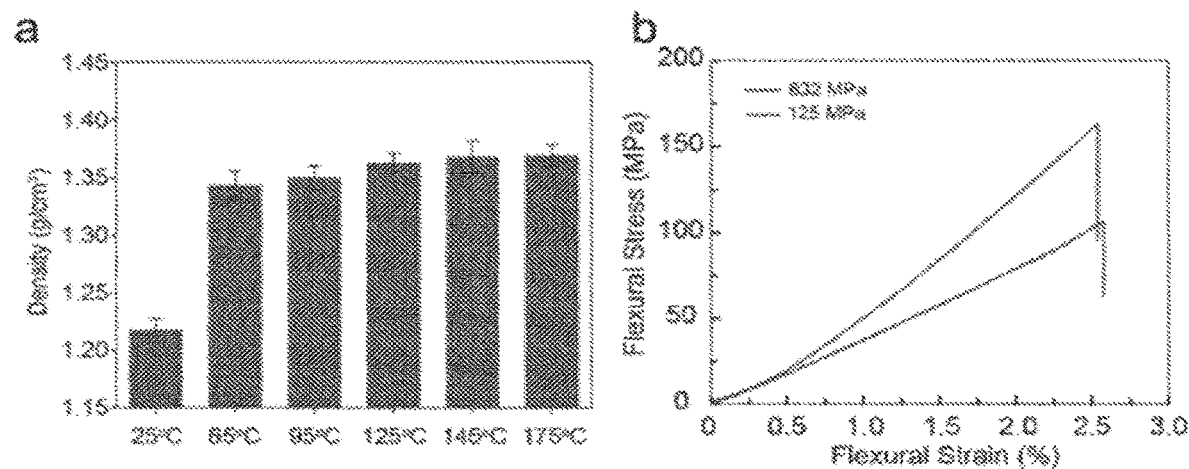

In another example, the role of pressure in the transformation of amorphous to silk structural materials was explored. At room temperature, the pressure-driven densification of raw amorphous silk materials introduces the formation of β-sheet structures (β-sheet content of ~10% versus ~1% for amorphous silk material, FIG. 8 panel B and D). When densification is carried out at elevated temperatures (65-175° C.), the density of the densified silk material reaches a constant value of ~1.35 g/cm$^3$ at high pressure (632 MPa) (FIG. 11, panel A). The densification under a lower external pressure shows a lower flexural strength in three-point bending test (FIG. 11, panel B). A combination of molecular structural (XRD, FTIR) and morphological analysis (SEM) revealed that increasing the processing temperature during densification facilitates the self-assembly of amorphous silk fibroin as indicated by the significant β-sheet structure formation at high temperatures (>145° C.). It is believed that the pressure- and heat-triggered structural transition in amorphous silk may help fuse the silk fibroin together, turning amorphous silk nanomaterials into a robust bulk material.

Example 4—Direct Molding Amorphous Silk Nanomaterials into Designed Shapes

Figure 12:
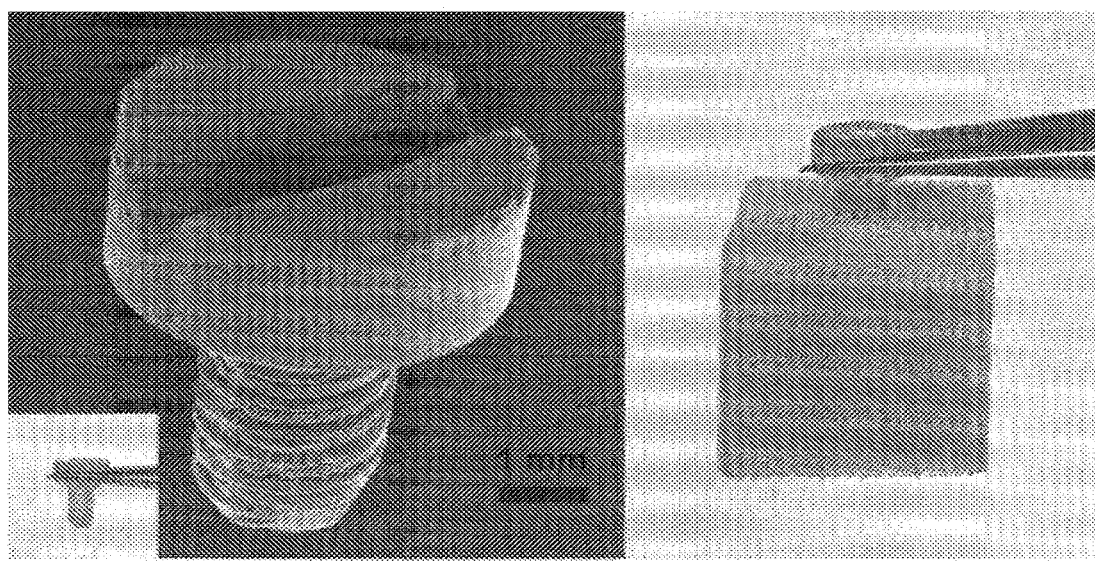
Figure 13A:
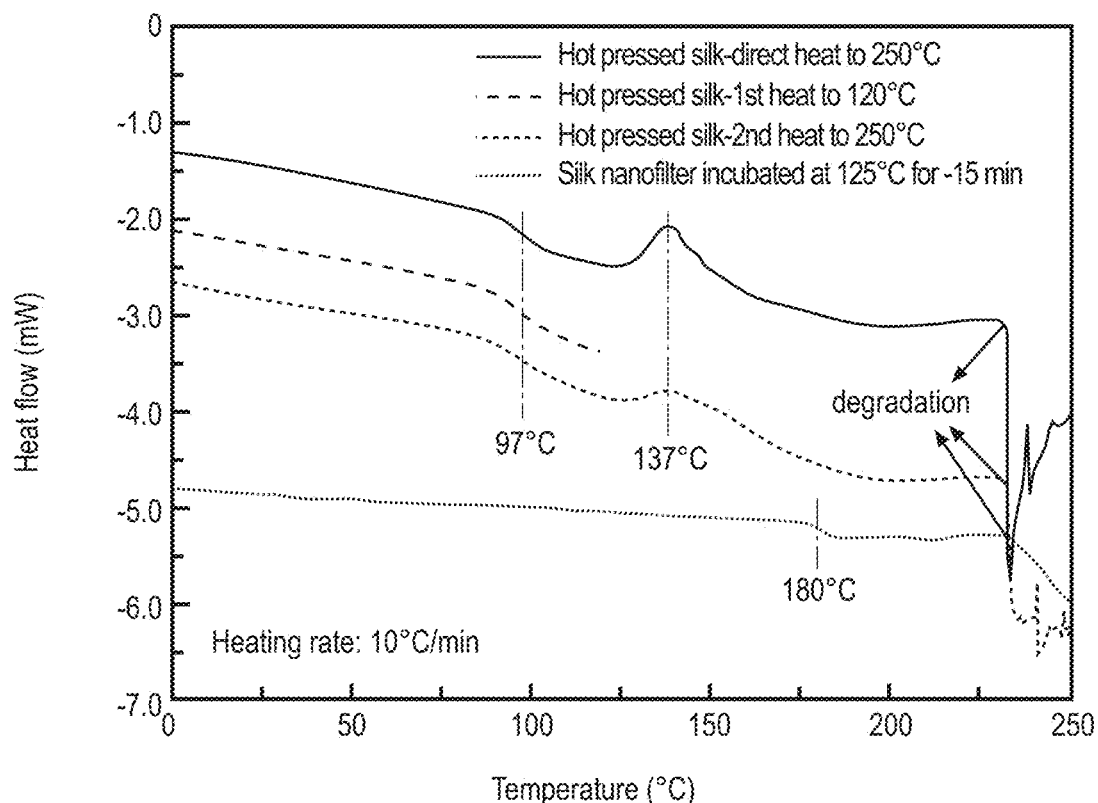
Figure 13B:
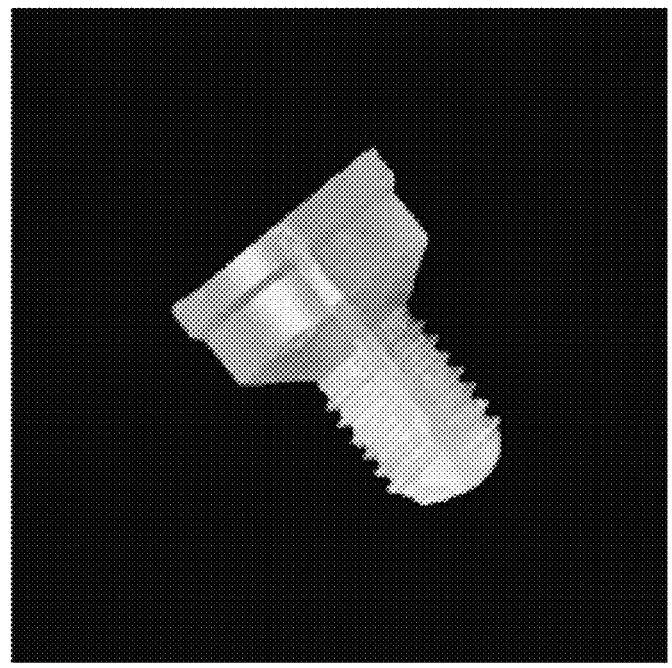
Figure 13C:
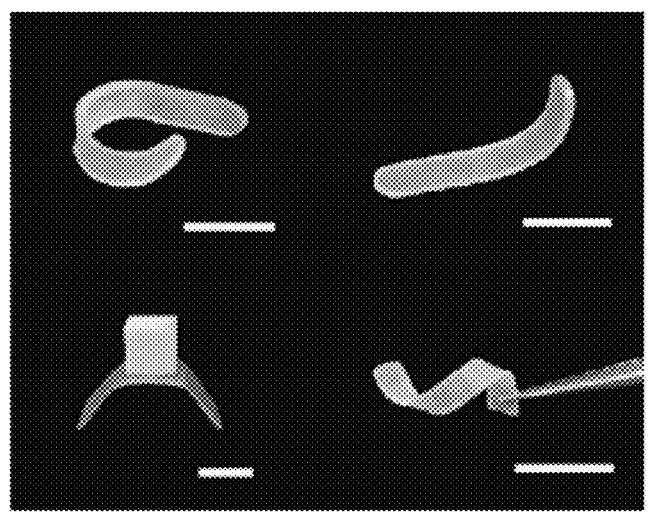
Figure 13D:
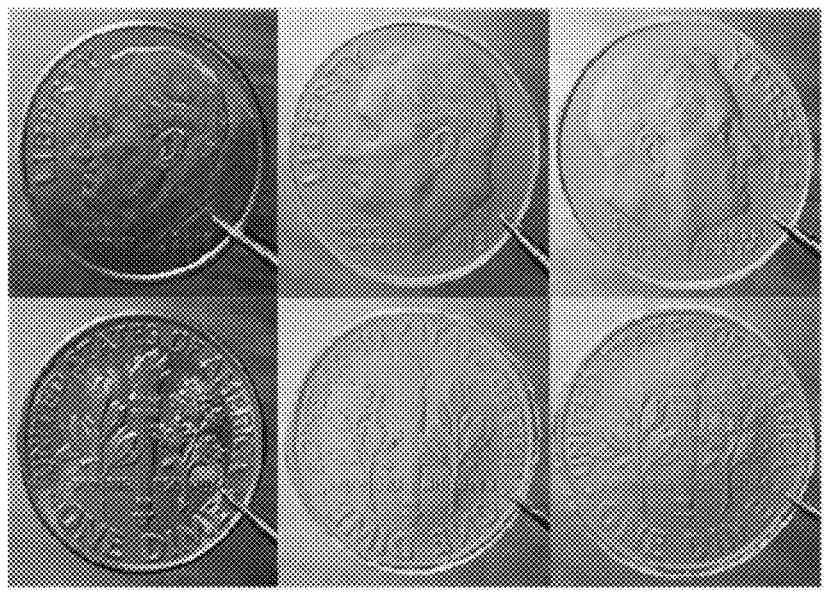
Figure 13E:
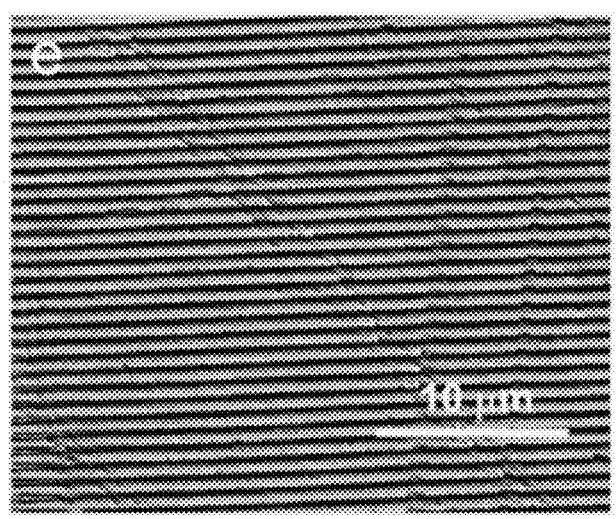

The amorphous silk materials can be loaded into predesigned mold for direct molding as shown in process B of FIG. 5. After molding, the silk materials are transformed into designed shape. In this case, the amorphous silk materials were filled into a mold in the shape of the screw, followed by molding the material into a shape at 120° C. and 800 MPa. The obtained silk screw is shown in FIG. 12.

Example 5—Thermal Forming and Patterning

In another example, a silk monolith obtained via heat and pressure can be used for thermal forming and patterning. Standard DSC was performed on silk plates obtained at 125° C. and 632 MPa (FIG. 13, panel A). The material showed a glass transition temperature (Tg) of 97° C., followed by an exothermic peak due to the crystallization of silk around 137° C. The silk plate contains significant amount of amorphous structure (~79% non-crystalline structure), which becomes flexible when the plate is heated above its Tg. This thermal softening property can be utilized to further mold the pre-pressed silk materials into desired shape, such as screw, patterns, and other complex shapes (FIG. 13, panels B-E). For example, to replicate the features of a dime coin, 200 mg of ASN are first pressed in a 13 mm die set at 700 MPa to make a small pellet. Then the pellet is placed on top a dime coin and heat compressed (100 MPa, 140° C.) to pattern the coin. FIG. 13 panel (D) shows the photographs of the patterned silk coin. Due to the transparence of the silk plate, the molded patterns are visible from both sides of the silk coin. Micro/nano structure patterning can be realized with using this method as well. FIG. 13, panel (E) show the SEM image of nanoscale patterned silk films.

Example 6—Engineering Silk Monolith Used for Machining into Designed Shapes

Figure 14:
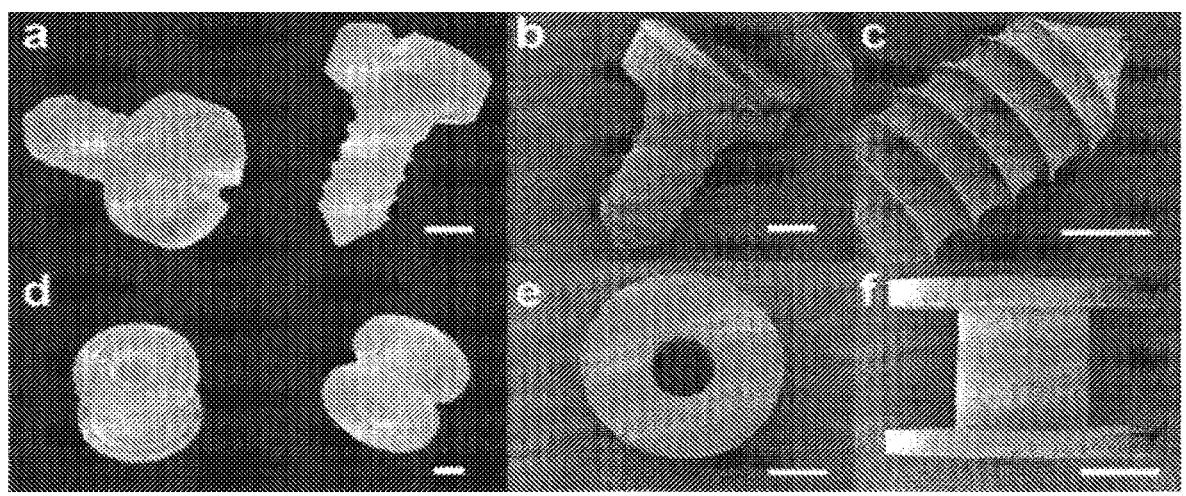

By applying different processing conditions, silk monolith with tunable molecular structures can be fabricated. More specifically, a silk monolith with low β-sheet content can be prepared at 95° C. and 632 MPa while a silk monolith with high β-sheet content can be prepared at 145° C. and 632 MPa. The silk monoliths can be further machined into designed shapes as shown in process A of FIG. 14. In this case, silk screws and ear tubes are machined from the silk monoliths. In addition, a water uptake test was carried out to investigate the swelling property of silk screws with different molecular structures.

Figure 16:
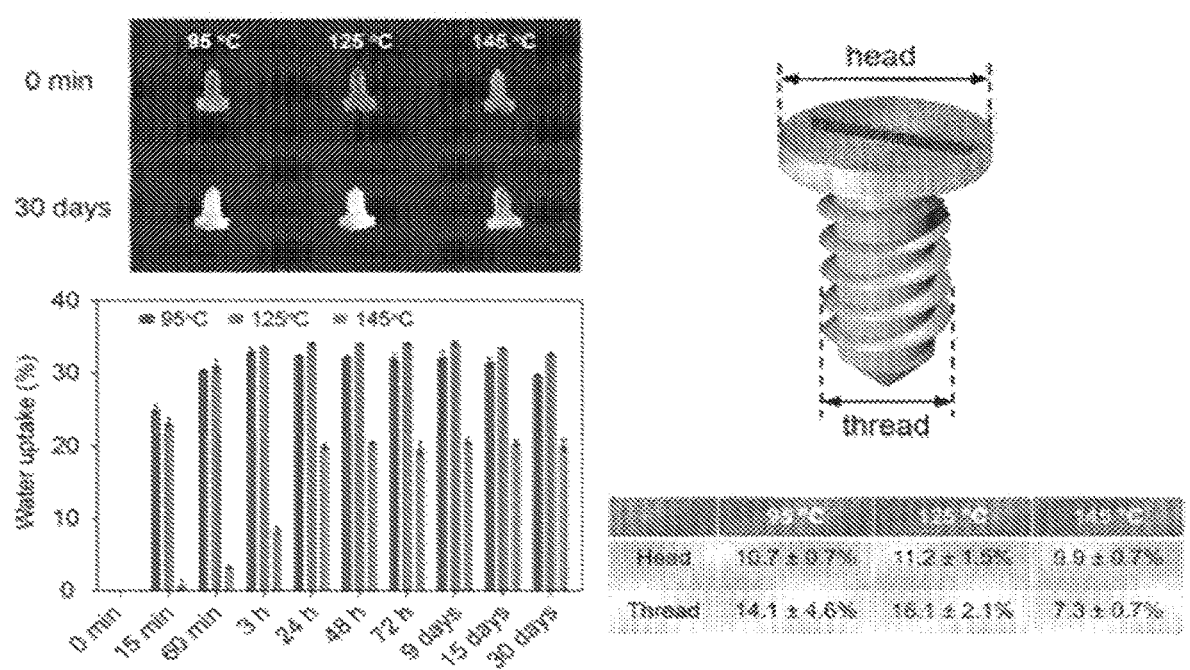

The swelling and degradability of these products can be controlled via manipulating processing conditions. In one example, silk-based bone screws were fabricated by machining silk bars prepared with different processing conditions (95° C. and 632 MPa; 125° C. and 632 MPa; 145° C. and 632 MPa) to vary the internal molecular structural features (β-sheet content and crystallinity). The degradation profiles showed that the degradability of the silk screws was tunable, where processing at 145° C. offered the slowest degradation rate in enzyme solutions over time (FIG. 15). It is noted that the silk screws processed at 95° C. and 125° C. show rapid degradation within 30 days with a weight loss of over 60% in 5 U/mL protease XIV solution. In addition, water uptake in PBS at 37° C. showed that the silk screws machined from silk bars prepared at 95° C. and 125° C. had a rapid water uptake within 15 min and a maximum of ~30 wt % (FIG. 16, panel B). In comparison, silk screws machined from silk bars prepared at 145° C. showed much slower water uptake with a maximum of ~20 wt %. These differences reflect the underlying control of crystalline content.

In addition, the degradation test showed that the degradability of silk screws is tunable where silk screws with a higher crystallinity offer lower degradation rate in both PBS and enzyme solution over the time period of 30 days (FIG. 15).

Example 7—Fabrication of Composite Materials Including Silk-Enzyme Composites

The methods described in previous examples can be extended to fabricate composite materials other than pure silk materials. Composite materials may include silk-small molecules system, silk-macromolecules system, silk-inorganic materials system, silk-hydrophobic/hydrophilic materials system, and/or silk-nanomaterials system, among others. In one example, dried silk powder was mixed with Protease XIV powders, an enzyme that degrades silk, to make silk-enzyme composite. The ratio of the Protease XIV was varied (0.2 wt %, 1.0 wt %, 5.0 wt %). Then the mixture was pressed in a 6 mm die set at 700 MPa to make small pellets. The prepared pellets were incubated in methanol for 48 hours to induce β-sheet structure in silk, enhancing the mechanical property and water-resistance.

Figure 17:
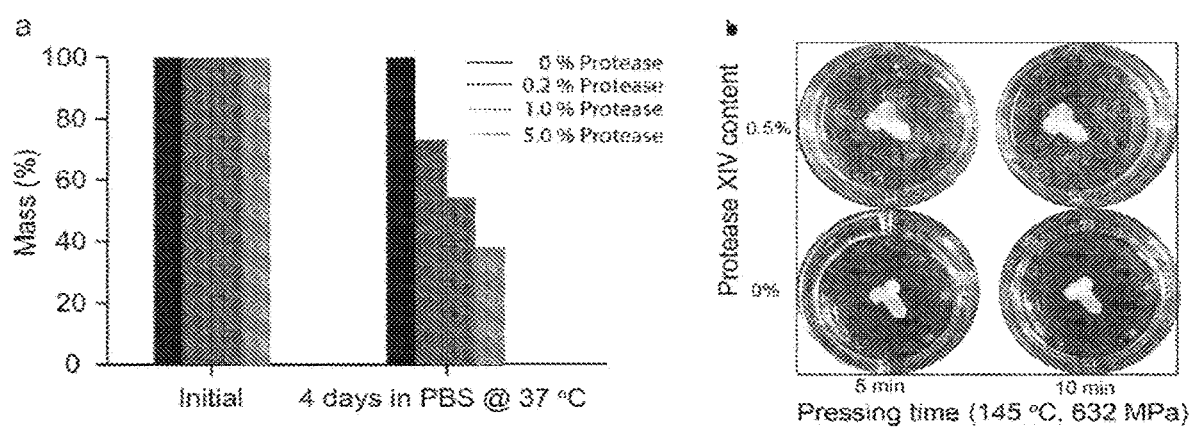
FIG. 17 shows an exemplary degradation profile of silk-Protease XIV composites (panel (a)) and images of silk-Protease XIV composites (panel (b)).

A degradation test was performed in PBS solution at 37° C. Results indicated that degradation of the silk material can be controlled by varying the ratio of Protease XIV in the composite. For instance, with a 5 wt % of Protease XIV loading ratio, the silk degrades 60 wt % after 4 days incubation in PBS solution at 37° C. (FIG. 17 panel (a)) whereas with a 0.2 wt % of Protease XIV loading ratio, the silk degrades about 30 wt %. Degradation of silk screws containing 0.5% Protease XIV machined from silk bars pressed at 145° C. and 632 MPa was observed (FIG. 16 panel (b)). It is noteworthy that the enzyme maintained its activity in the silk/enzyme system during the heat pressing (145° C. and 632 MPa), which otherwise would be lost without the presence of silk. This suggests that silk can stabilize enzyme at elevated temperature and pressure. These methods demonstrate the ability to fabricate silk-based bulk materials with controllable degradability.

A component added to the silk matrix/article may be an organic or inorganic molecule. A component may be incorporated into silk matrix by mixing silk solution with the component and then lyophilizing the solution. A component may include but is not limited to micro/nanomaterials such as metal micro/nanomaterials, graphene, graphene oxide, and/or hydroxyapatite.

A component may be added to create a fiber-reinforced silk matrix/article. Natural or synthetic fibers can be incorporated into silk matrix by using the described method. Natural or synthetic fibers may include raw silk fibers, synthetic nylon fibers and/or synthetic polymer fibers.

Example 8—Fabrication of Composite Materials Including Silk-Graphene Composites

Figure 18:
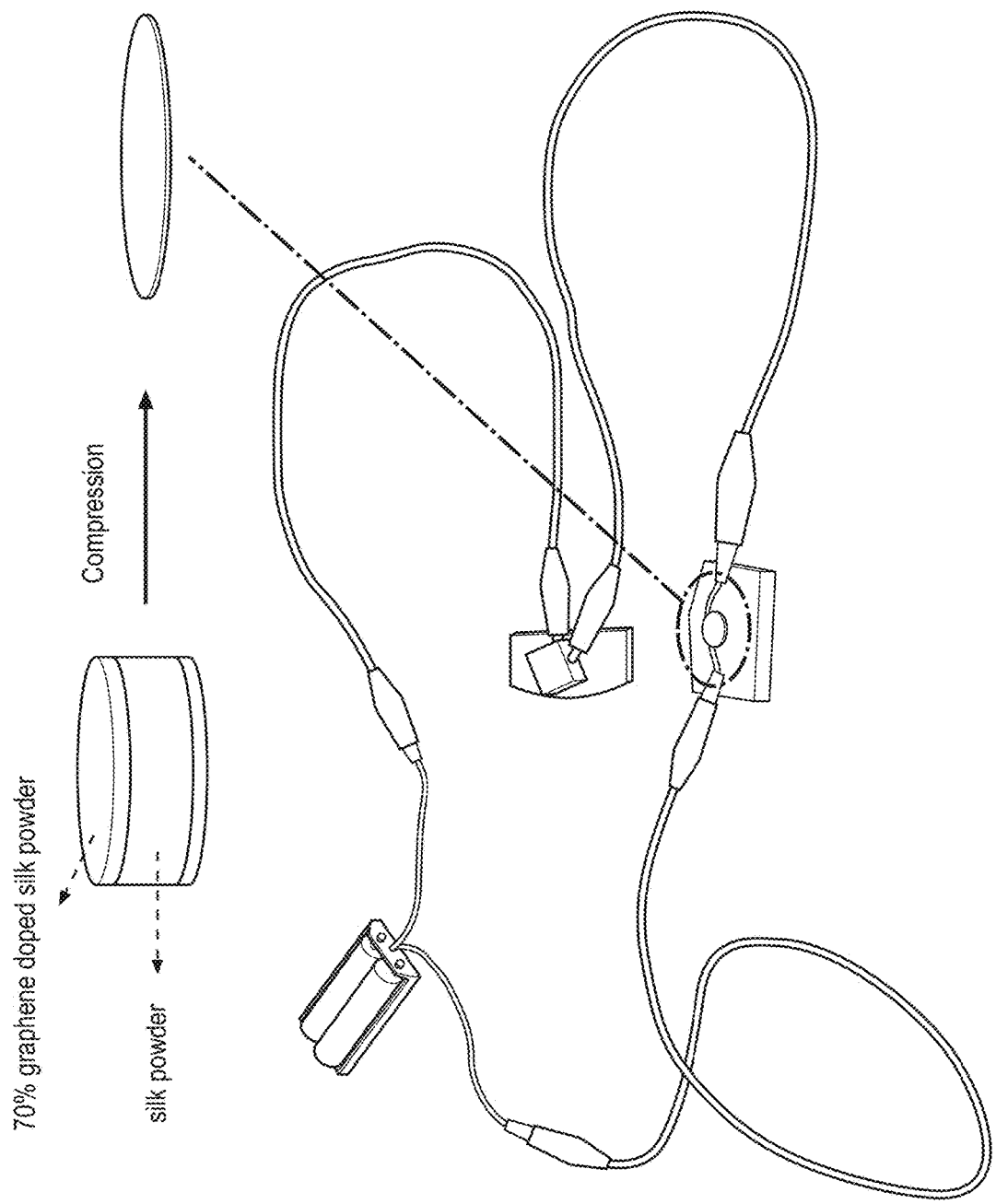
FIG. 18 shows an exemplary conductivity test of silk-graphene film.

In this example, the lyophilized silk material was used to fabricate a silk-graphene composite. Graphene is hydrophobic and it is difficult to make silk-graphene composite with solution method directly. However, using the methods described in previous examples, silk-graphene composite materials were formed by mixing graphene and silk powders in solid state. In one instance, graphene was mixed with fine silk powder with a loading ratio of 70.0 wt %. The mixture was then pressed in a 6 mm die set at 700 MPa to make compressed silk-graphene films. The as prepared silk-graphene film is highly conductive and shows great potential in fabricating bioelectronics (FIG. 18).

Example 9—Examining Structural Differences Between Lyophilized Silk and Solid Silk Articles In this Example, certain structural features of lyophilized silk and solid silk articles subjected to high temperature and pressure as described herein were examined.

Figure 19:
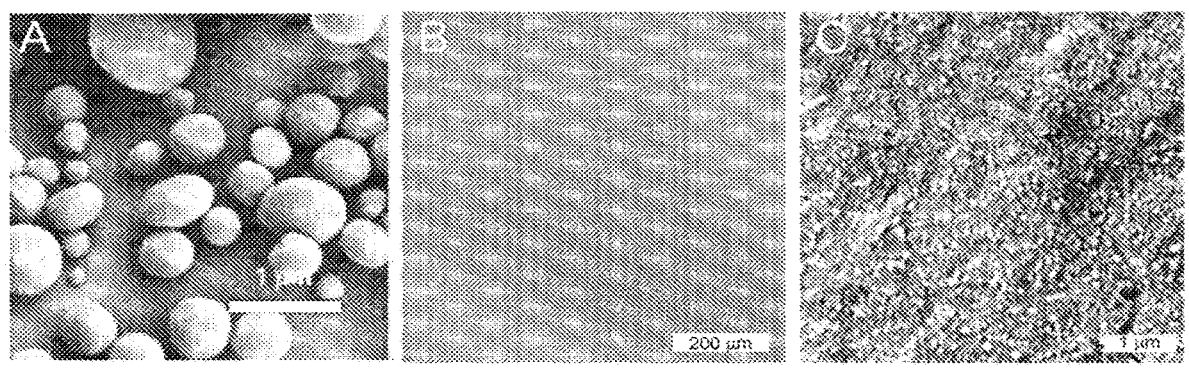
FIG. 19 shows SEM images of silk fibroin materials including lyophilized silk powder shown in panel (A) and the inner structure of an silk article pressed at 145° C., 632 MPa for 15 minutes in panel (B) and shown further magnified in panel (C).

FIG. 19 panel (A) shows the SEM images of lyophilized silk powder. The inner structure of an silk article pressed at 145 □C, 632 MPa for 15 minutes are shown in FIG. 19 panel (B) and panel (C). The loose lyophilized silk powders transformed into a solid silk article. The close-up view of the inner structure of the silk article (FIG. 19 panel C) revealed globular features in the nanometer range. These features show similarity to globular structures in the natural silkworm and spider silk fibers. SEM images indicate raw lyophilized silk material undergoes a fusion process is not a simple physical compaction of the raw silk powder to become the pressed silk article of FIG. 19 panel (B) and panel (C). The molecular conformation of silk partially transformed from random coil/amorphous state to crystalline β-sheet structure. It appears that the observed level of homogeneity in the structure of these pressed silk articles was unachievable by using previous methods and is only possible using the methods described herein.

Example 10—Methods of Transforming Silk into New Materials

Materials and chemicals. Sodium carbonate, lithium bromide, protease XIV and chymotrypsin were purchase from Sigma-Aldrich (Sigma-Aldrich, St. Louis, MO) and used as received.

Regenerated silk fibroin preparation. *Bombyx mori* (*B. mori*) cocoons were cut into small pieces and boiled in an aqueous 0.02 M $Na_2CO_3$ (Sigma-Aldrich, USA) for 30 min, followed by rinsing in distilled water to remove the $Na_2CO_3$ and sericin. The degummed silk was allowed to dry overnight at room temperature. The dried silk was dissolved in 9.3 M LiBr solution at 60° C. for 3-4 h. The solution was subsequently dialyzed for 3 days in distilled water using Slide-A-Lyzer dialysis cassettes (MWCO 3,500, Pierce, USA). The water was changed five times during the dialysis (1 h, 4 h, 8 h, 24 h, 48 h). After dialysis, the solution was centrifuged for 10 min at 13,000 rpm to remove insoluble impurities. The concentration of the final silk solution was determined by measuring a volume of solution and the final dried weight (~6 w/v %). The solution was diluted with distilled water and frozen in liquid nitrogen. The frozen silk was then lyophilized at −80° C. until complete sublimation. The lyophilized silk was milled into fine powders and stored in ambient dry conditions to prevent any rehydration of the lyophilized solids until used in the processing steps below.

Hot pressing of amorphous silk nanomaterials (ASN). ASN was packed into predesigned mold, followed by hot pressing at 632 MPa and variable temperatures (25° C., 65° C., 95° C., 125° C., 145° C., 175° C.) for 15 min. After hot pressing, the samples were cooled down to room temperature and used for characterizations.

Thermal analysis. The thermal degradation of silk samples was measured by thermogravimetric analysis (TGA) from 30 to 800° C. in $N_2$ (99.99%) with a scanning speed of 5° C./min. For all measurements, samples were kept under $N_2$ in the furnace to reach a stable weight prior to heating. Differential scanning calorimetry (DSC) measurements were carried out on a TA Instruments Q100 DSC (TA Instruments, New Castle, DE) under a dry nitrogen gas flow of 50 mL/min with samples encapsulated in aluminum pans. Both standard DSC and temperature-modulated DSC (TMDSC) measurements were performed. In standard DSC measurements, the samples was heated from −50 to 200° C. with a heating rate of 10° C./min. In TMDSC measurements, the samples were heated from −50 to 200° C. at 10° C./min with a modulation period of 60 s and temperature amplitudes of 1.59° C.

Scanning electron microscopy (SEM). The morphology of the scaffolds was characterized by scanning electron microscopy (SEM) (Ultra55 field-emission scanning electron microscope, Carl Zeiss AG, Harvard University Center for Nanoscale Systems). The SEM images were collected with a voltage of 5 kV and the samples were sputter coated with a thin layer of gold.

Fourier-transform Infrared spectroscopy (FTIR). Fourier-transform Infrared spectroscopy (FTIR) was carried out on a JASCO FTIR 6200 spectrometer (JASCO, Tokyo, Japan) equipped with a MIRacle attenuated total reflectance (ATR) Ge crystal cell in absorbance mode. For each measurement, the spectrum was recorded with 32 scans and a resolution of 4.0 $cm^{-1}$. The protein secondary structure contents were determined by performing peak deconvolution over the amide I region (1600-1700 $cm^{-1}$). The numbers and positions of peaks were defined from the results of second derivative spectra and fixed during the deconvolution process. A Gaussian model was selected for the band shape and the bandwidth, which was automatically adjusted by the software.

X-ray diffraction. X-ray diffraction was carried out at SAXSLAB small angle/wide angle X-ray scattering system (MIT Center for Materials Science and Engineering). The wavelength of the X-ray beam was 1.5409 Å, with a fixed energy of 45 kV. The sample-to-detector distance is 109.1 mm and an exposure time of 60 s was used in the experiment.

Three-point bending test. The three-point bending tests were carried out on an Instron 3366 machine (Instron, Norwood, USA) in flexural test mode at 25° C. and 50% RH with a loading rate of 0.2 mm/min and 2 mm/min for unnotched dry specimen and wet specimens, respectively. The specimen has a length of 12 mm, a width of 7 mm and a thickness of 1 mm.

In vitro water uptake and swelling test. Machined silk screws (n=4 per condition) were placed in 37° C. phosphate-buffered saline (PBS) for various amounts of time (0 min, 15 min, 60 min, 3 h, 24 h, 48 h, 72 h, 9 days, 15 days, and 30 days) and observed for changes in weight and diameter to signify fluid uptake and swelling. Surface moisture was removed from the sample by wiping with a Kimwipe (Kimberly-Clark, USA), the wet weight of the sample taken (Ws) and the head and thread diameters were measured. The water uptake (%) was calculated.

$$\text{Water uptake (\%)}=[(Ws-Wd)/Ws]\times 100 \quad (1)$$

In vitro enzymatic degradation test. Machined silk screws (n=3 per condition) were incubated at 37° C. in 2 mL solution of 5 U/mL Protease XIV and 40 U/mL Chymotrypsin in PBS or in PBS as a negative control. The solutions were changed every 2-3 days. At designated time points (2 days, 5 days, 10 days, 20 days, 30 days) groups of samples were rinsed in DI water and dried before weighting. The remaining mass of each sample was collected and SEM image of the samples were collected.

Figure 20:
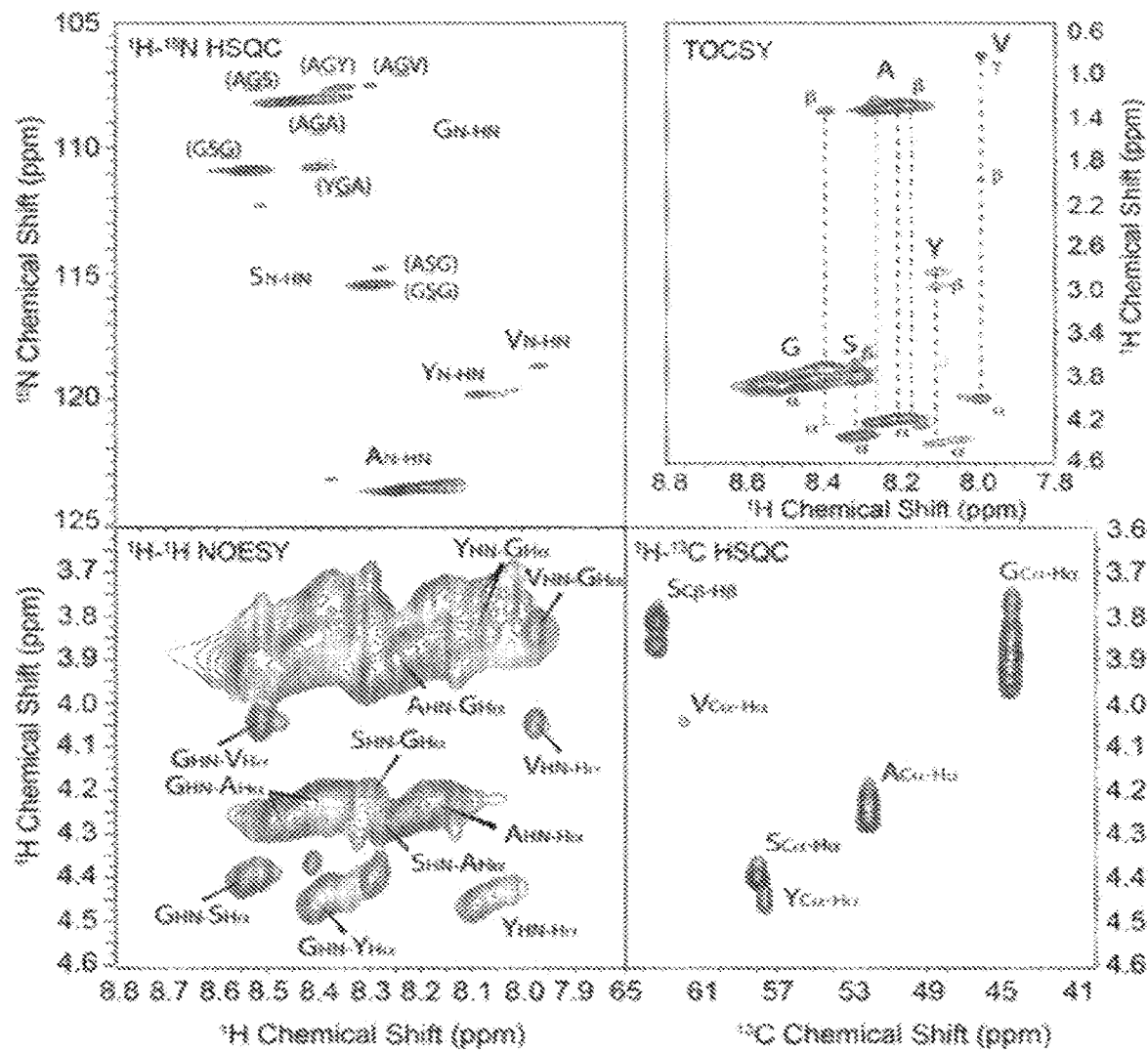
FIG. 20 shows the solution NMR spectra of regenerated aqueous silk solution (6 wt %).
Figure 21:
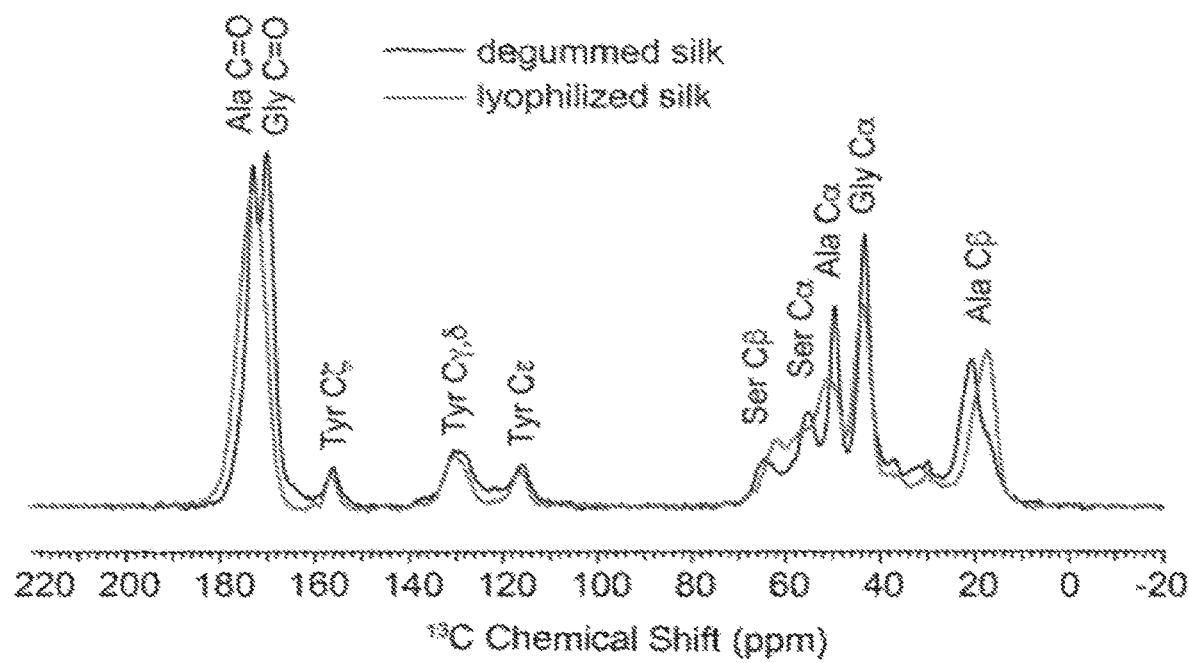
FIG. 21 shows $^{13}C$ cross polarization-magic angle spinning (CP-MAS) spectra of natural degummed silk and lyophilized silk.

NMR spectra of regenerated aqueous silk solution (6 wt %). Solution NMR experiments were performed on a Bruker 850 MHz Avance IIIHD spectrometer equipped with a 5 mm cryogenically helium-cooled triple-resonance TCL Cryo-Probe. The Larmor frequency of 1H, 13C, and 15N were 850.28 MHz, 213.82 MHz, and 86.17 MHz. A sealed capillary containing D2O was used for NMR locking. NOESY was performed with a mixing time of 150 ms, 11 ppm spectral width and in both t1 and t2 dimensions, 512 and 2048 complex points in t1 and t2 dimension, 16 scans and a relaxation delay of 1 s. TOCSY was performed with a mixing time of 60 ms, 11 ppm spectral width and in both t1 and t2 dimensions, 512 and 2048 complex points in t1 and t2 dimension, 16 scans and a relaxation delay of 1 s. 1H-13C HSQC was collected with 165.8 ppm spectra width in t1 and 11 ppm in t2 dimensions, 256 and 1024 complex points in t1 and t2, 64 scans. 1H-15N HSQC was collected with 28.0 ppm spectra width in t1 and 11 ppm in t2 dimensions, 512 and 1024 complex points in t1 and t2, 32 scans. The NMR data were processed and analyzed using MestReNova. FIG. 20 shows the solution NMR spectra of regenerated aqueous silk solution (6 wt %).

$^{13}$C cross polarization-magic angle spinning (CP-MAS) spectra of natural degummed silk and lyophilized silk. The spectra were collected on a Varian VNMRS 400 MHz spectrometer equipped with a 3.2 mm triple-resonance probe operating in double-resonance ($^1$H/$^{13}$C) mode. The CP condition for $^1$H$\pi^{13}$C CP-MAS experiments consisted of a 2.25 µs $^1$H π/2 pulse, followed by a 1.0 ms ramped (3%) 1H spin-lock pulse of 70 kHz radio frequency (rf) field strength. The experiments were performed with a 25 kHz sweep width, a recycle delay of 3.0 s, 8192 scans and a two-pulse phase-modulated (TPPM) 1H decoupling level of 91 kHz at a MAS speed of 20 kHz for all samples. FIG. 23 shows $^{13}$C cross polarization-magic angle spinning (CP-MAS) spectra of natural degummed silk and lyophilized silk.

Example 11—In Vitro Degradation Analysis of Silk Ear Tubes with or without Protease XIV Doping The methods described in previous examples were used to fabricate pure silk and silk-Protease XIV composite ear tubes. The ear tubes were machined from pure silk and silk-protease XIV composite bulk materials that were prepared under two different conditions: at a temperature of 125° C. and a pressure of 632 MPa; and at a temperature of 145° C. and a pressure of 632 MPa.

A degradation test was performed in PBS solution at 37° C. for different lengths of time: 5 minutes, 1 hour, 3 hours, 6 hours, 24 hours, 48 hours, and 72 hours. Results are shown in FIG. 30.

References. The following list of references are identified in the above disclosure by the number immediately preceding the reference and not by the paragraph number located within the brackets.

1. Altman, G. H. et al. Silk-based Biomaterials. Biomaterials 24, 401-416 (2003).
2. Kundu, B., Rajkhowa, R., Kundu, S. C. & Wang, X. Silk fibroin biomaterials for tissue regenerations. Advanced Drug Delivery Reviews 65, 457-470 (2013).
3. Koh, L.-D. et al. Structures, mechanical properties and applications of silk fibroin materials. Prog. Polym. Sci. 46, 86-110 (2015).
4. Vepari, C. & Kaplan, D. L. Silk as a biomaterial. Prog. Polym. Sci. 32, 991-1007 (2007).
5. Zhou, C. et al. Silk Fibroin: Structural Implications of a Remarkable Amino Acid Sequence. Proteins: Struct., Funct., Genet. 44, 119-122 (2001).
6. Marsh, R. E., Corey, R. B. & Pauling, L. An Investigation of the Structure of Silk Fibroin. Biochim. Biophys. Acta 16, 1-34 (1955).
7. Lefèvre, T., Rousseau, M.-E. & Pézolet, M. Protein Secondary Structure and Orientation in Silk as Revealed by Raman Spectromicroscopy. Biophys. J. 92, 2885-2895 (2007).
8. Cebe, P. et al. Beating the Heat—Fast Scanning Melts Silk Beta Sheet Crystals. Sci. Rep. 3, 741-7 (2013).
9. Sidhu, M. S., Kumar, B. & Singh, K. P. The processing and heterostructuring of silk with light. Nat. Mater. 16, 938-945 (2017).
10. Pauling, L. & Corey, R. B. Configurations of Polypeptide Chains with Favored Orientations Around Single Bonds: Two New Pleated Sheets. Proc. Natl. Acad. Sci. U.S.A. 37, 729-740 (1951).
11. Cheng, G., Wang, X., Tao, S., Xia, J. & Xu, S. Differences in regenerated silk fibroin prepared with different solvent systems: From structures to conformational changes. Journal of Applied Polymer Science 132, n/a-n/a (2015).
12. Um, I. C., Kweon, H., Park, Y. H. & Hudson, S. Structural characteristics and properties of the regenerated silk fibroin prepared from formic acid. Int. J. Biol. Macromol. 29, 91-97 (2001).
13. Ha, S.-W., Tonelli, A. E. & Hudson, S. Structural studies of Bombyx mori silk fibroin during regeneration from solutions and wet fiber spinning. Biomacromolecules 6, 1722-1731 (2005).
14. Trabbic, K. A. & Yager, P. Comparative structural characterization of naturally- and synthetically-spun fibers of Bombyx mori fibroin. Macromolecules 31, 462-471 (1998).
15. Ha, S.-W., Park, Y. H. & Hudson, S. Dissolution of Bombyx mori silk fibroin in the calcium nitrate tetrahydrate-methanol system and aspects of wet spinning of fibroin solution. Biomacromolecules 4, 488-496 (2003).
16. Rockwood, D. N. et al. Materials fabrication from Bombyx mori silk fibroin. Nat. Protoc. 6, 1612-1631 (2011).
17. Perrone, G. S. et al. The use of silk-based devices for fracture fixation. Nat. Commun. 5, 1-9 (2014).
18. Li, C. et al. Regenerated silk materials for functionalized silk orthopedic devices by mimicking natural processing. Biomaterials 110, 24-33 (2016).
19. Yamaguchi, K. et al. Primary Structure of the Silk Fibroin Light Chain Determined by cDNA Sequencing and Peptide analysis. J. Mol. Biol. 210, 127-139 (1989).
20. Wray, L. S. et al. Effect of processing on silk-based biomaterials: reproducibility and biocompatibility. J. Biomed. Mater. Res. Part B Appl. Biomater. 99, 89-101 (2011).
21. Marelli, B. et al. Programming function into mechanical forms by directed assembly of silk bulk materials. Proc. Natl. Acad. Sci. USA 114, 451-456 (2017).
22. Kluge, J. A., Kahn, B. T., Brown, J. E., Omenetto, F. G. & Kaplan, D. L. Optimizing molecular weight of lyophilized silk as a shelf-stable source material. ACS Biomater. Sci. Eng. 2, 595-605 (2016).
23. Hu, X., Kaplan, D. & Cebe, P. Determining Beta-Sheet Crystallinity in Fibrous Proteins by Thermal Analysis and Infrared Spectroscopy. Macromolecules 39, 6161-6170 (2006).
24. Lu, Q. et al. Silk Self-Assembly Mechanisms and Control From Thermodynamics to Kinetics. Biomacromolecules 13, 826-832 (2012).
25. Koebley, S. R. et al. Silk Reconstitution Disrupts Fibroin Self-Assembly. Biomacromolecules 16, 2796-2804 (2015).
26. Krywka, C., Krasnov, I., Figuli, R., Burghammer, M. & Müller, M. Determination of silkworm silk fibroin compressibility using high hydrostatic pressure with in situ X-ray microdiffraction. Macromolecules 47, 7187-7193 (2014).
27. Hu, X.; Kaplan, D.; Cebe, P. Thermochim. Acta 2007, 461 (1-2), 137-144.
28. Hu, X.; Kaplan, D.; Cebe, P. Macromolecules 2008, 41, 3939-3948.

Equivalents and Scope. The recitation of a listing of elements in any definition of a variable herein includes definitions of that variable as any single element or combinations (or sub-combinations) of listed elements. The recitation of an embodiment herein includes that embodiment as any single embodiment or in combination with any other embodiments or portions thereof. Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A silk fibroin article comprising semi-crystalline silk fibroin, wherein the silk fibroin article has a glass transition temperature between about 40° C. to 120° C., wherein a flexural strength of the silk fibroin article is at least 5 MPa and density of the entire silk fibroin article is at least 1.20 g/cm$^3$.

2. The silk fibroin article of claim 1, wherein the silk fibroin article is homogenous.

3. The silk fibroin article of claim 1, wherein the silk fibroin article is transparent.

4. The silk fibroin article of claim 1, wherein the silk fibroin article is at least one of macro-patterned, micro-patterned, or nano-patterned.

5. The silk fibroin article of claim 1, wherein the silk fibroin article comprises at least one additive to form a composite silk article.

6. The silk fibroin article of claim 5, wherein the at least one additive comprises at least one of small organic or inorganic molecules, an organic macromolecule, an inorganic macromolecule, a biological macromolecule; an electrically conductive material, a carbon-based material, antibodies and antigen-binding fragments thereof; an antigen; a nucleic acid; nucleic acid analogs and derivatives; a sugar; an immunogen; natural compounds and extraction from biological systems, cells, bacterias, or tissues; a synthetic material; a metallic material; an alloy; a hydrophobic material; a hydrophilic material; or a nanomaterial.

7. The silk fibroin article of claim 6, wherein the at least one additive is the organic macromolecule, and wherein the organic macromolecule is or comprises at least one enzyme.

8. The silk fibroin article of claim 7, wherein the at least one enzyme comprises at least one of Protease XIV, Proteinase K, a-chymotrypsin, collagenase, matrix metalloproteinase-1 (MMP-1) or MMP-2.

9. The silk fibroin article of claim 7, wherein an activity of the at least one enzyme is stabilized by silk at elevated temperature and pressure.

10. The silk fibroin article of claim 6, wherein the at least one additive is the electrically conductive material, wherein the electrically conductive material comprises at least one of an inorganic conductive material, an organic conductive material, a metal, an alloy, a semiconductor material, or a conjugated polymer.

11. The silk fibroin article of claim 5, wherein the at least one additive is mixed with the semi-crystalline silk fibroin at a ratio between 0.001 wt % and 95.0 wt %.

12. The silk fibroin article of claim 1, wherein the silk fibroin article degrades at least 1 wt % after 30 days of exposure to an aqueous environment at 37° C.

13. The silk fibroin article of claim 1, wherein the silk fibroin article is bioresorbable.

14. The silk fibroin article of claim 1, wherein the silk fibroin article has thermal forming properties and can be reformed to desirable shapes at elevated temperatures or elevated pressures.

15. The silk fibroin article of claim 1, wherein the silk fibroin article is or comprises a packaging material.

16. The silk fibroin article of claim 15, wherein the packaging material is suitable for use in fabricating electronic devices, drug delivery system, patterning, molding, and any combination thereof.

* * * * *